United States Patent [19]

Yoshioka et al.

[11] Patent Number: 5,797,844
[45] Date of Patent: Aug. 25, 1998

[54] METHOD AND APPARATUS FOR ULTRASONIC IMAGING AND ULTRASONIC IMAGE PROCESSING

[75] Inventors: Hideki Yoshioka; Kazuhiro Iinuma, both of Tokyo, Japan

[73] Assignee: Kabushiki Kaisha Toshiba, Kawasaki, Japan

[21] Appl. No.: 701,058

[22] Filed: Aug. 21, 1996

[30] Foreign Application Priority Data

Aug. 23, 1995 [JP] Japan .................. 7-214920

[51] Int. Cl.⁶ .................................. A61B 8/00
[52] U.S. Cl. ............................. 600/442; 73/631
[58] Field of Search .............. 128/660.06, 660.05, 128/661.09, 660.01, 661.04, 661.1; 600/442–443; 73/631

[56] References Cited

U.S. PATENT DOCUMENTS 5,014,711  5/1991  Nagasaki ........................ 600/443
5,540,228  7/1996  Li ..................................... 600/443
5,579,768  12/1996  Klesenski ...................... 128/600.06

*Primary Examiner*—Francis Jaworski
*Attorney, Agent, or Firm*—Foley & Lardner

[57] ABSTRACT

An ultrasonic image processing for accurately detecting the annulus portion from the ultrasonic image of the long axis view of a heart. A heart wall contour is extracted from the ultrasonic image, and a center of gravity of the heart wall contour is determined. Then, for an image imaged from an apex portion side, the annulus portion is detected from points on the heart wall contour located at positions deeper than the center of gravity, whereas for an image imaged by a transesophageal echocardiography, the annulus portion is detected from points on the heart wall contour located at positions shallower than the center of gravity. An ultrasonic image can be obtained in high precision by correcting the sensitivity in a direction perpendicular to the ultrasonic beam, either by adjusting a reception gain or correcting an image intensity at specific positions within a scanning space, according to an angle formed by an ultrasonic beam vector passing through each specific position and a prescribed vector defined at each specific position.

35 Claims, 34 Drawing Sheets

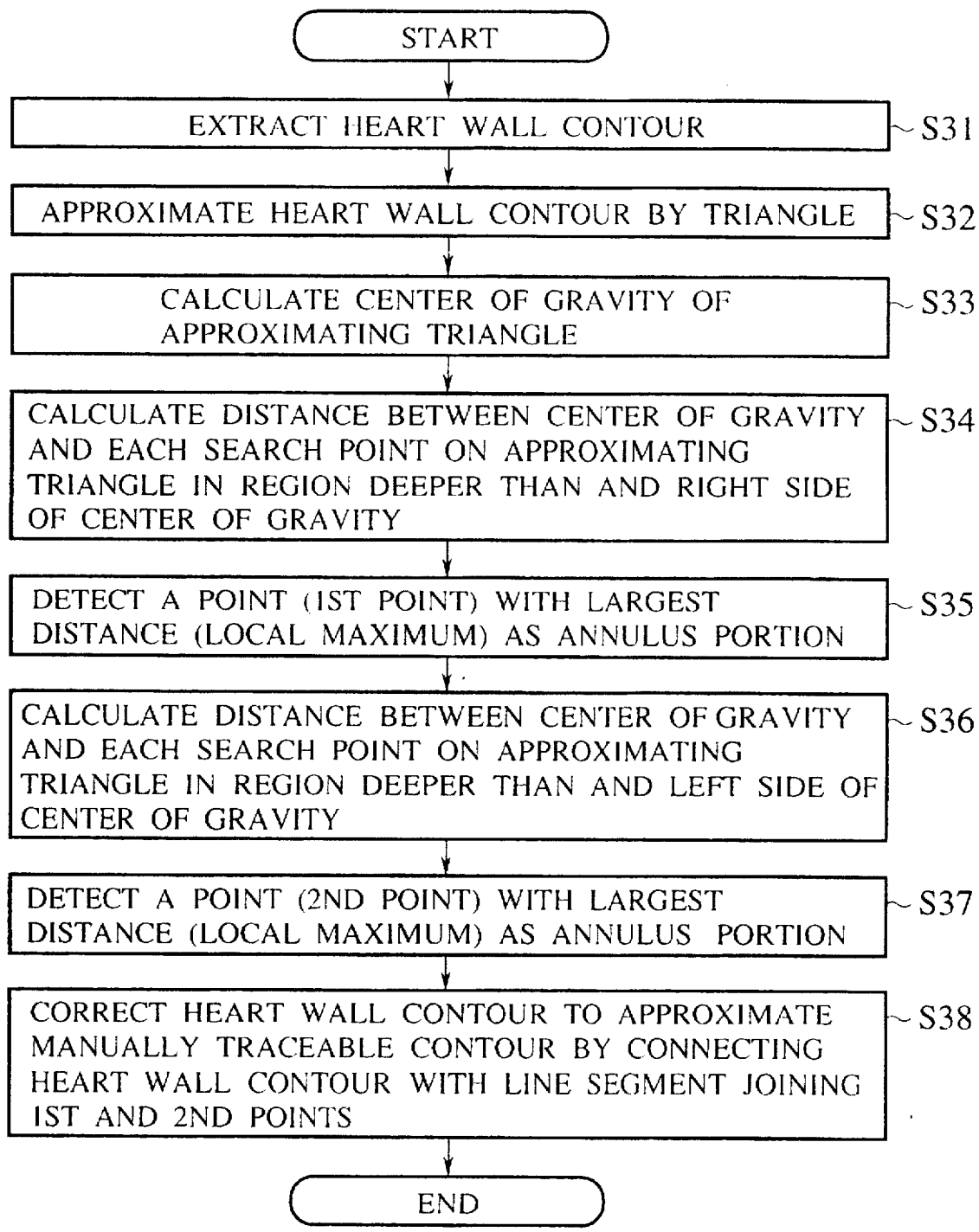

FIG.32
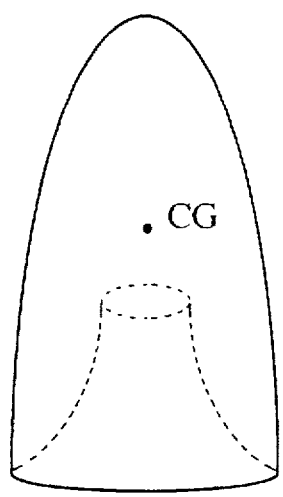
FIG.33A  FIG.33B
 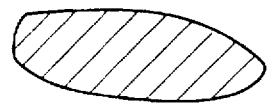
FIG.34
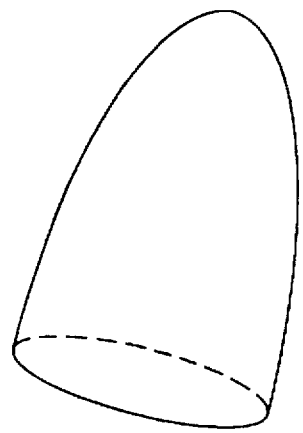

CORRECTION SIGNAL GENERATOR 35

ARBITRARY SHAPE U

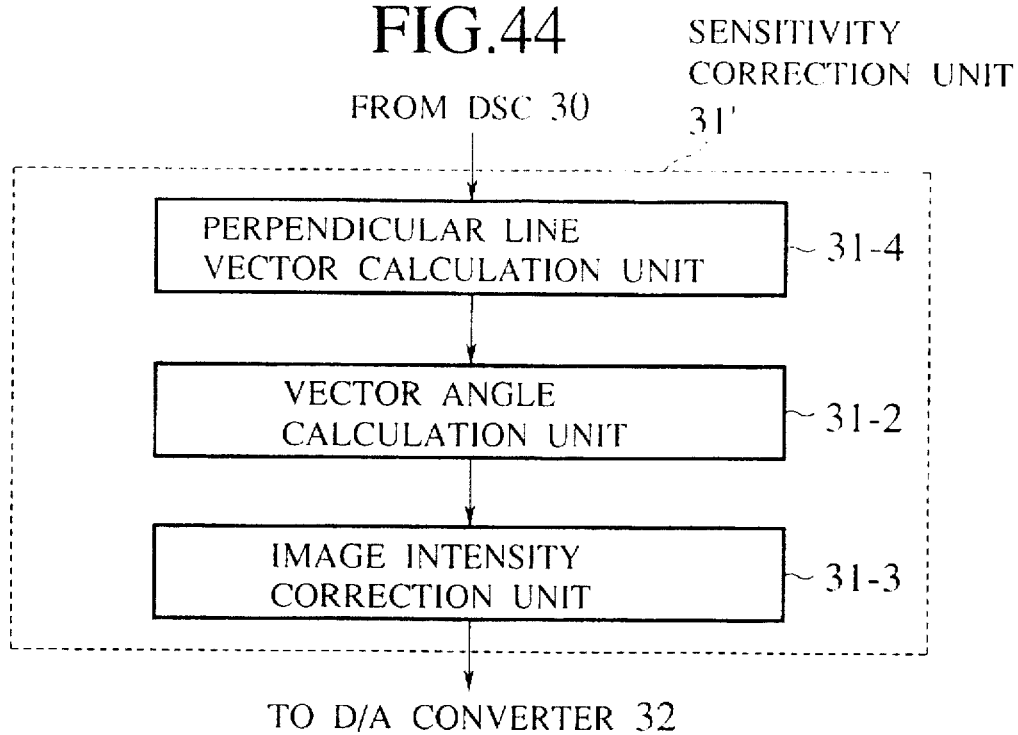

METHOD AND APPARATUS FOR ULTRASONIC IMAGING AND ULTRASONIC IMAGE PROCESSING

BACKGROUND OF THE INVENTION

1. Field of the Invention

The present invention relates to an ultrasonic imaging apparatus for acquiring internal information on a body to be examined by applying ultrasonic beams onto a body to be examined, and an ultrasonic image processing method for detecting an annulus portion from an ultrasonic image of a long axis view of a heart imaged from an apex portion (apex of heart).

2. Description of the Background Art

In recent years, due to the change of our eating habits, heart disease is steadily increasing, and it is now the second major cause of death in Japan, second only to cancer. In particular, there is a significant increase in ischemic heart disease such as the angina pectoris and the myocardial infarction and the disease called cardiomyopathy, and accordingly there is a great demand for an early and thorough diagnosis of such heart diseases.

The diagnosis of these heart diseases and the monitoring of the cardiac function are usually made by obtaining the ultrasonic images of a heart, extracting heart wall contours in the obtained ultrasonic images, and evaluating a heart pumping function (cardiac function) or a local wall motion according to an area, a volume, and their changes obtained from the heart wall contours. For references, FIG. 1 shows an outward appearance of a mitral valve with an annulus portion in the heart, while FIG. 2 shows an exemplary long axis view of a heart viewed from an apex portion (apical view).

A method for extracting the heart wall contour can be largely classified into a manual tracing method, an automatic tracing method, and a semi-automatic tracing method which requires some manual operations such as that for specifying a starting point of a contour tracing.

FIG. 3A shows the heart wall contour obtained by the manual tracing method, FIG. 3B shows the heart wall contour obtained by the automatic tracing method, and FIG. 3C shows the heart wall contour obtained by the semi-automatic tracing method. The automatic tracing method of FIG. 3B is a method for tracing the heart wall contour by following an edge of the heart wall and sequentially connecting lines. The semi-automatic tracing method of FIG. 3C is a method for approximating the heart wall contour by gradually expanding a heart wall contour model pattern such as SNAKES disclosed in M. Kass. et al.: Int. J. Computer Vision, Vol. 1, pp. 321–831, 1988. In this semi-automatic tracing method, there is a need to manually specify an initial position of the model pattern, but because of the use of the model pattern which has the contour like shape from the beginning, there is an advantage that a gap in the mitral valve can be connected by a smooth shape despite the fact that there is no edge information.

It should be noted that, in the manual tracing method, it is customary among the physicians to trace heart wall contour in a simplified form in which the annulus portions are joined by a straight line segment as shown in FIG. 3A, rather than closely tracing a complicated shape of the mitral valve.

The cardiac function information, such a an area and a volume, are measured according to the heart wall contour. Consequently, there is an inevitable difference between the measurement result according to the manual tracing method which obtains the contour in a simplified form with the annulus portions joined by a straight line segment, and the measurement result according to the automatic tracing method or the semi-automatic tracing method which traces the annulus portions faithfully.

Note that the automatic tracing method or the semi-automatic tracing method is only intended as an optional substitution for the manual tracing method. On the other hand, it is usually very useful to compare the newly obtained measurement result with the past measurement results.

However, the fact that there can be a difference due to different tracing methods used in obtaining the measurement results is very problematic as it can give rise to a possibility of erroneous diagnosis. In this regard, in view of the frequency by which each tracing method is actually used by the physician and the work load of the physician, it is preferable to make the heart wall contour obtained by the automatic or semi-automatic tracing method to resemble that obtained by the manual tracing method.

In other words, it is necessary for the automatic or semi-automatic tracing method to obtain the heart wall contour in a simplified form in which the annulus portions are joined by a straight line segment, and to this end, it is indispensable for the automatic or semi-automatic tracing method to be capable of detecting the annulus portions in the ultrasonic image.

The ultrasonic imaging apparatus is an apparatus for imaging internal information of a body to be examined by applying ultrasonic beams generated from a probe onto an interior of the body to be examined, receiving reflected beams returned from the interior of the body to be examined, and processing the resulting electric signals. The ultrasonic beams have a natural property of being attenuated by dispersion, absorption, and scattering, so that the sensitivity naturally becomes poorer for a deeper interior portion of the body to be examined which requires a longer propagation time for the ultrasonic beams.

In order to compensate for this natural deterioration of the sensitivity, the sensitivity of the ultrasonic imaging apparatus is usually increased in proportion to the time elapsed since the ultrasonic beam transmission. In other words, the ultrasonic imaging apparatus uses the so called TCG (Time Gain Control) technique which uses a higher reception gain for reflected beams from a deeper place, or the so called AGC (Automatic Gain Control) technique which changes the sensitivity according to a magnitude of the received signal. These sensitivity corrections are related to a direction parallel to the ultrasonic beams.

On the other hand, the ultrasonic imaging apparatus is associated with a poor sensitivity regarding a direction perpendicular to the ultrasonic beams in principle, because it utilizes reflected beams of the ultrasonic beams, but no sensitivity correction related to a direction perpendicular to the ultrasonic beams has been used in a conventional ultrasonic imaging apparatus.

Consequently, there have been cases in which the poor sensitivity in the direction perpendicular to the ultrasonic beams causes a "lack" of the image as shown in FIG. 4, which can adversely affect the diagnosis using the ultrasonic image. For example, in a case of diagnosing heart disease by using the ultrasonic imaging apparatus, there have been cases in which the contour of the heart cannot be comprehended accurately because of this "lack" of the image.

SUMMARY OF THE INVENTION

It is therefore an object of the present invention to provide a method and an apparatus for ultrasonic image processing, which are capable of accurately detecting the annulus portion from the ultrasonic image of the long axis view of a heart.

It is another object of the present invention to provide a method and an apparatus for ultrasonic image processing, which are capable of automatically obtaining the heart wall contour in a simplified form in which two annulus portions are joined by a straight line segment, similar to the manual tracing method.

It is another object of the present invention to provide a method and an apparatus for ultrasonic imaging, which are capable of obtaining the ultrasonic image in high precision by correcting the sensitivity in a direction perpendicular to the ultrasonic beam.

According to one aspect of the present invention there is provided a method for processing an ultrasonic image of a long axis view of a heart imaged from an apex portion side, comprising the steps of: extracting a heart wall contour from the ultrasonic image; determining a center of gravity of the heart wall contour extracted by the extracting step; and detecting an annulus portion of the heart from a plurality of points on the heart wall contour located at positions deeper than the center of gravity determined by the determining step, according to a prescribed criterion regarding said plurality of points.

According to another aspect of the present invention there is provided a method for processing an ultrasonic image of a long axis view of a heart imaged by a transesophageal echocardiography, comprising the steps of: extracting a heart wall contour from the ultrasonic image; determining a center of gravity of the heart wall contour extracted by the extracting step; and detecting an annulus portion of the heart from a plurality of points on the heart wall contour located at positions shallower than the center of gravity determined by the determining step, according to a prescribed criterion regarding said plurality of points.

According to another aspect of the present invention there is provided a method for processing an ultrasonic image of a long axis view of a heart, comprising the steps of: extracting a heart wall contour from the ultrasonic image; determining a center of gravity of the heart wall contour extracted by the extracting step; and detecting an annulus portion of the heart from a plurality of points on the heart wall contour located at positions father away from an apex portion on the heart wall contour than the center of gravity determined by the determining step, according to a prescribed criterion regarding said plurality of points.

According to another aspect of the present invention there is provided an apparatus for processing an ultrasonic image of a long axis view of a heart imaged from an apex portion side, comprising: means for extracting a heart wall contour from the ultrasonic image; means for determining a center of gravity of the heart wall contour extracted by the extracting means; and means for detecting an annulus portion of the heart from a plurality of points on the heart wall contour located at positions deeper than the center of gravity determined by the determining means, according to a prescribed criterion regarding said plurality of points.

According to another aspect of the present invention there is provided an apparatus for processing an ultrasonic image of a long axis view of a heart imaged by a transesophageal echocardiography, comprising: means for extracting a heart wall contour from the ultrasonic image; means for determining a center of gravity of the heart wall contour extracted by the extracting means; and means for detecting an annulus portion of the heart from a plurality of points on the heart wall contour located at positions shallower than the center of gravity determined by the determining means, according to a prescribed criterion regarding said plurality of points.

According to another aspect of the present invention there is provided an apparatus for processing an ultrasonic image of a long axis view of a heart, comprising: means for extracting a heart wall contour from the ultrasonic image; means for determining a center of gravity of the heart wall contour extracted by the extracting means; and means for detecting an annulus portion of the heart from a plurality of points on the heart wall contour located at positions father away from an apex portion on the heart wall contour than the center of gravity determined by the determining means, according to a prescribed criterion regarding said plurality of points.

According to another aspect of the present invention there is provided a method for imaging an ultrasonic image, comprising the steps of: obtaining an ultrasonic image of an object to be imaged by applying an ultrasonic beam to the object and receiving a reflected beam from the object; and adjusting a reception gain used by the obtaining step at specific positions within a scanning space scanned by the ultrasonic beam, according to an angle formed by an ultrasonic beam vector defined by the ultrasonic beam passing through each specific position and a prescribed vector defined at each specific position.

According to another aspect of the present invention there is provided a method for imaging an ultrasonic image, comprising the steps of: obtaining an ultrasonic image of an object to be imaged by applying an ultrasonic beam to the object and receiving a reflected beam from the object; and correcting an image intensity of the ultrasonic image obtained by the obtaining step at specific positions within a scanning space scanned by the ultrasonic beam, according to an angle formed by an ultrasonic beam vector defined by the ultrasonic beam passing through each specific position and a prescribed vector defined at each specific position.

According to another aspect of the present invention there is provided an apparatus for imaging an ultrasonic image comprising: means for obtaining an ultrasonic image of an object to be imaged by applying an ultrasonic beam to the object and receiving a reflected beam from the object; and means adjusting a reception gain used by the obtaining means at specific positions within a scanning space scanned by the ultrasonic beam, according to an angle formed by an ultrasonic beam vector defined by the ultrasonic beam passing through each specific position and a prescribed vector defined at each specific position.

According to another aspect of the present invention there is provided an apparatus for imaging an ultrasonic image, comprising: means for obtaining an ultrasonic image of an object to be imaged by applying an ultrasonic beam to the object and receiving a reflected beam from the object; and means for correcting an image intensity of the ultrasonic image obtained by the obtaining means at specific positions within a scanning space scanned by the ultrasonic beam, according to an angle formed by an ultrasonic beam vector defined by the ultrasonic beam passing through each specific position and a prescribed vector defined at each specific position.

Other features and advantages of the present invention will become apparent from the following description taken in conjunction with the accompanying drawings.

BRIEF DESCRIPTION OF THE DRAWINGS

FIG. 13 is a flow chart for the operation of the ultrasonic image processing apparatus of FIG. 5 in a third mode.

FIG. 32 is an illustration of an exemplary three-dimensional heart wall contour that can be handled by the ultrasonic image processing apparatus of FIG. 5.

FIGS. 33A and 33B are illustrations of an exemplary valve ring portion detected from the three-dimensional heart wall contour of FIG. 32.

FIG. 34 is an illustration of an exemplary corrected three-dimensional heart wall contour obtained by the ultrasonic image processing apparatus of FIG. 5.

FIG. 44 is a block diagram of an internal configuration of a sensitivity correction unit in an ultrasonic imaging apparatus according to a fifth embodiment of the present invention.

FIG. 45 is a block diagram of an internal configuration of a correction signal generator in an ultrasonic imaging apparatus according to a fifth embodiment of the present invention.

DETAILED DESCRIPTION OF THE PREFERRED EMBODIMENTS

Referring now to FIG. 5 through FIG. 34, the first embodiment of the present invention will be described in detail. This first embodiment is directed to a method and an apparatus for ultrasonic image processing.

Figure 5:
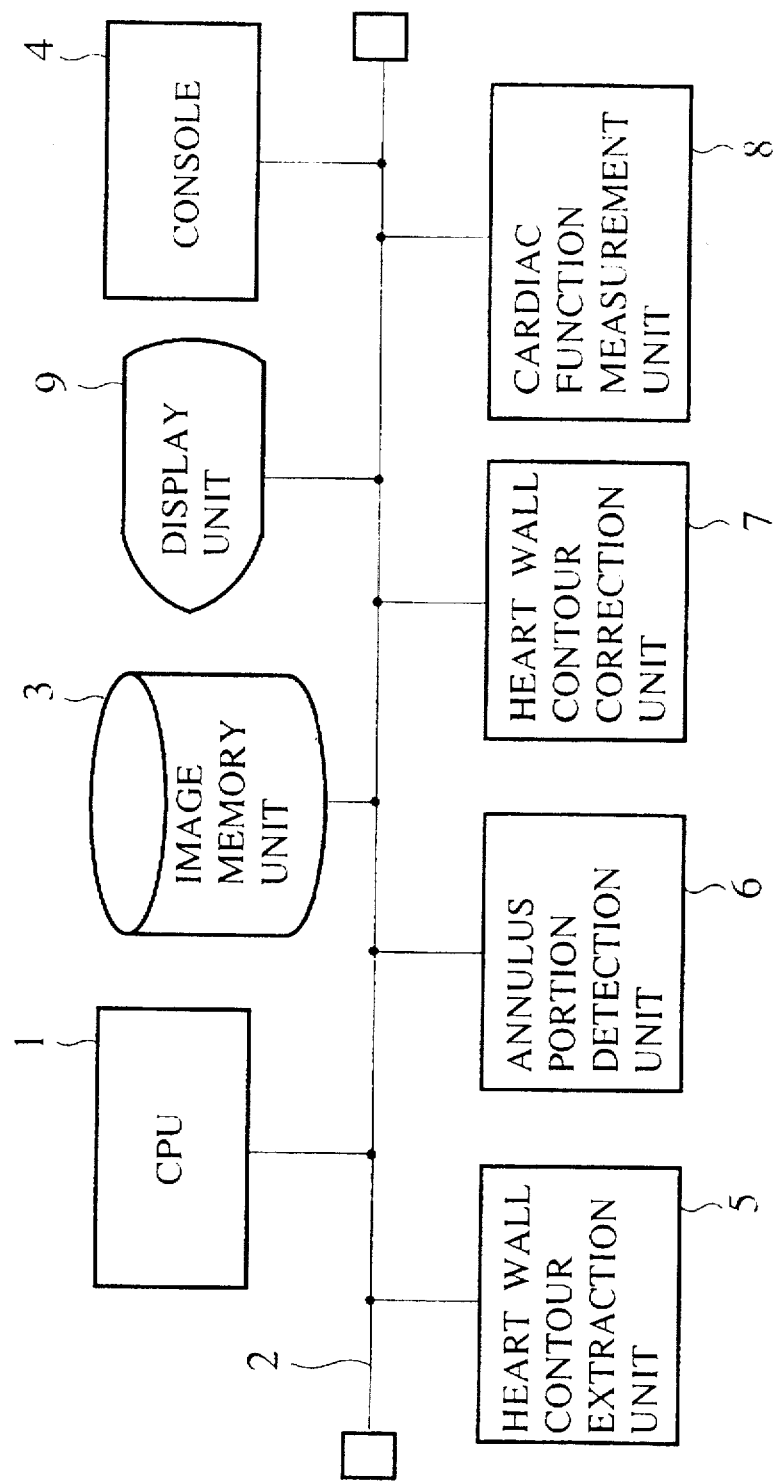
FIG. 5 is a block diagram of an ultrasonic image processing apparatus according to a first embodiment of the present invention.

An ultrasonic image processing apparatus according to this first embodiment has a configuration as shown in FIG. 5, which comprises a CPU 1, an image memory unit 3, a console 4, a heart wall contour extraction unit 5, an annulus portion detection unit 6, a heart wall contour correction unit 7, a cardiac function measurement unit 8, and a display unit 9, all of which are connected through a control/data bus 2.

Figure 1:
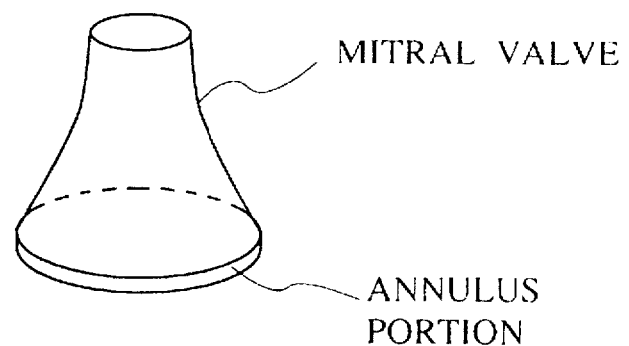
FIG. 1 is a perspective view of a mitral valve of a heart.
Figure 2:
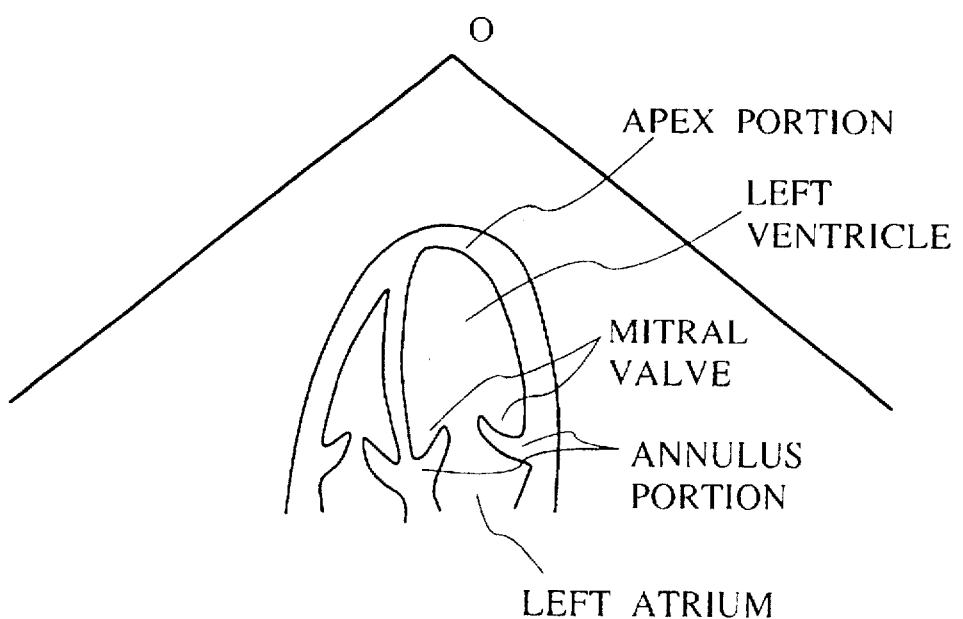
FIG. 2 is an illustration of an ultrasonic image showing an exemplary cross sectional view of a long axis view of a heart viewed from an apex portion.

The image memory unit 3 stores in advance at least one frame part of the ultrasonic image data reconstructed by an ultrasonic imaging apparatus (not shown). Here, each ultrasonic image is in a form of a structural tomographic image (B mode image) of a long axis view of a heart imaged from an apex portion, such as that shown in FIG. 2. As is well known to those skilled in the art, this ultrasonic image expresses the annulus portion at a position deeper than the apex portion, viewing from a position 0 (a transmission/reception position) of an ultrasonic probe (not shown), because of the consideration to desirable contact position and angle of the ultrasonic probe with respect to the chest portion of the body to be examined, and position and orientation of the heart with respect to the contact position and angle.

Figure 3A:
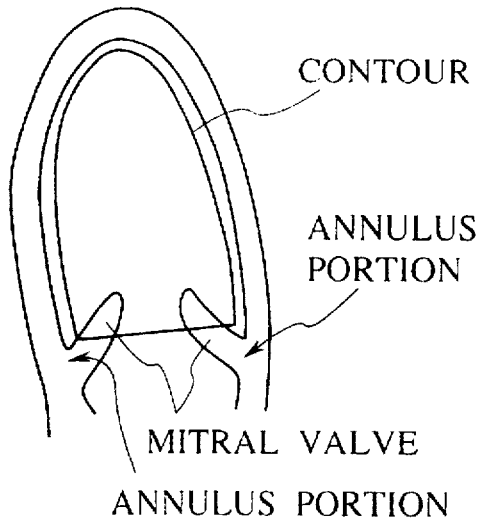
FIG. 3A is an illustration showing an exemplary heart wall contour obtained by the manual tracing method.
Figure 3B:
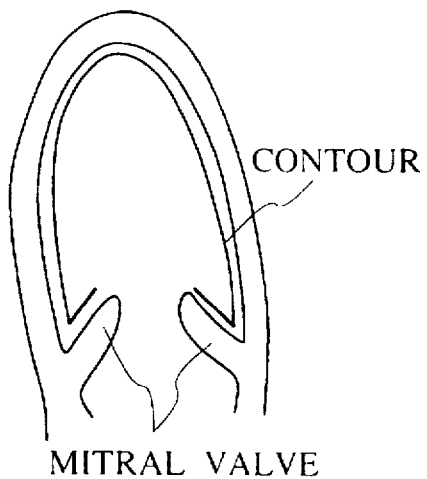
FIG. 3B is an illustration showing an exemplary heart wall contour obtained by the automatic tracing method.
Figure 3C:
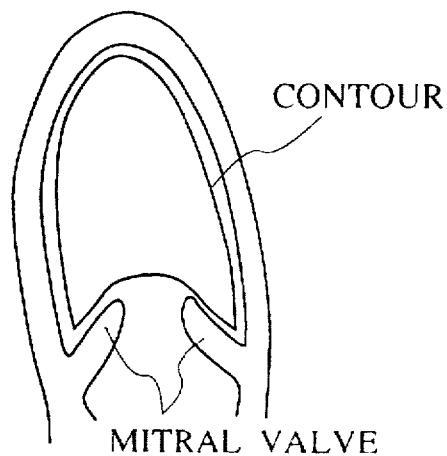
FIG. 3C is an illustration showing an exemplary heart wall contour obtained by the semi-automatic tracing method.
Figure 4:
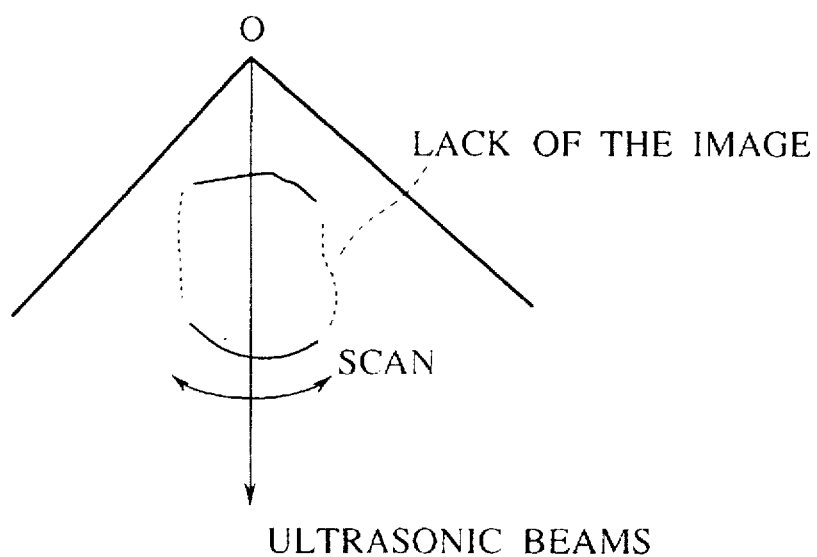
FIG. 4 is an illustration of an ultrasonic image showing a "lack" of the image.

The heart wall contour extraction unit 5 extracts the heart wall contour from this type of ultrasonic image, based on the automatic tracing method shown in FIG. 3B or the semi-automatic tracing method shown in FIG. 3C. Here, the automatic tracing method is a method for tracing the heart wall contour by following an edge of the heart wall and sequentially connecting lines, whereas the semi-automatic tracing method is a method for approximating the heart wall contour by gradually expanding a heart wall contour model pattern such as SNAKES disclosed in M. Kass. et al.: Int. J. Computer Vision. Vol. 1, pp. 321–331, 1988. The heart wall contour extracted by the automatic tracing method or the semi-automatic tracing method expresses the contour of the mitral valve faithfully.

The annulus portion detection unit 6 detects the annulus portion from the heart wall contour extracted by the heart wall contour extraction unit 5. A procedure for detecting the annulus portion in this annulus portion detection unit 6 will be described in detail below.

The heart wall contour correction unit 7 corrects the heart wall contour extracted by the heart wall contour extraction unit 5 according to the annulus portion detected by the annulus portion detection unit 6, so as to make it resemble the heart wall contour obtainable in the manual tracing method. Here, the heart wall contour obtainable in the manual tracing method is in a simplified form in which the annulus portions are joined by a straight line segment as shown in FIG. 3A, rather than closely tracing a complicated shape of the mitral valve.

The cardiac function measurement unit 8 measures the cardiac function such as a heart pumping function or a local wall motion mainly according to an area, a volume, and their changes obtained from the heart wall contours corrected by the heart wall contour correction unit 7.

The display unit 9 displays the ultrasonic image, the extracted heart wall contour, the detected annulus portions, the corrected heart wall contour, the measured cardiac function information, and other necessary information.

Now, the operation in the ultrasonic image processing apparatus of FIG. 5 will be described. In the following, processing up to correction of heart wall contour, i.e., up to the completion of the heart wall contour approximating the heart wall contour obtainable in the manual tracing method, will be described first, and then processing for cardiac function measurement will be described.

The former processing includes processing for detecting the annulus portion from the heart wall contour extracted by the heart wall contour extraction unit 5, and this annulus portion detection processing includes five types of operation modes. In this first embodiment, the ultrasonic image processing apparatus may allow the operator to select a desired one of these five operation modes, or may selectively set one of these five operation modes. Each of these five operation modes will now be described one by one.

First mode

The first mode deals with the heart wall contour obtained by the automatic tracing method in which two tip ends of the mitral valve are not joined, and does not deal with the heart wall contour obtained by the semi-automatic tracing method in which two tip ends of the mitral valve are joined.

Figure 6:
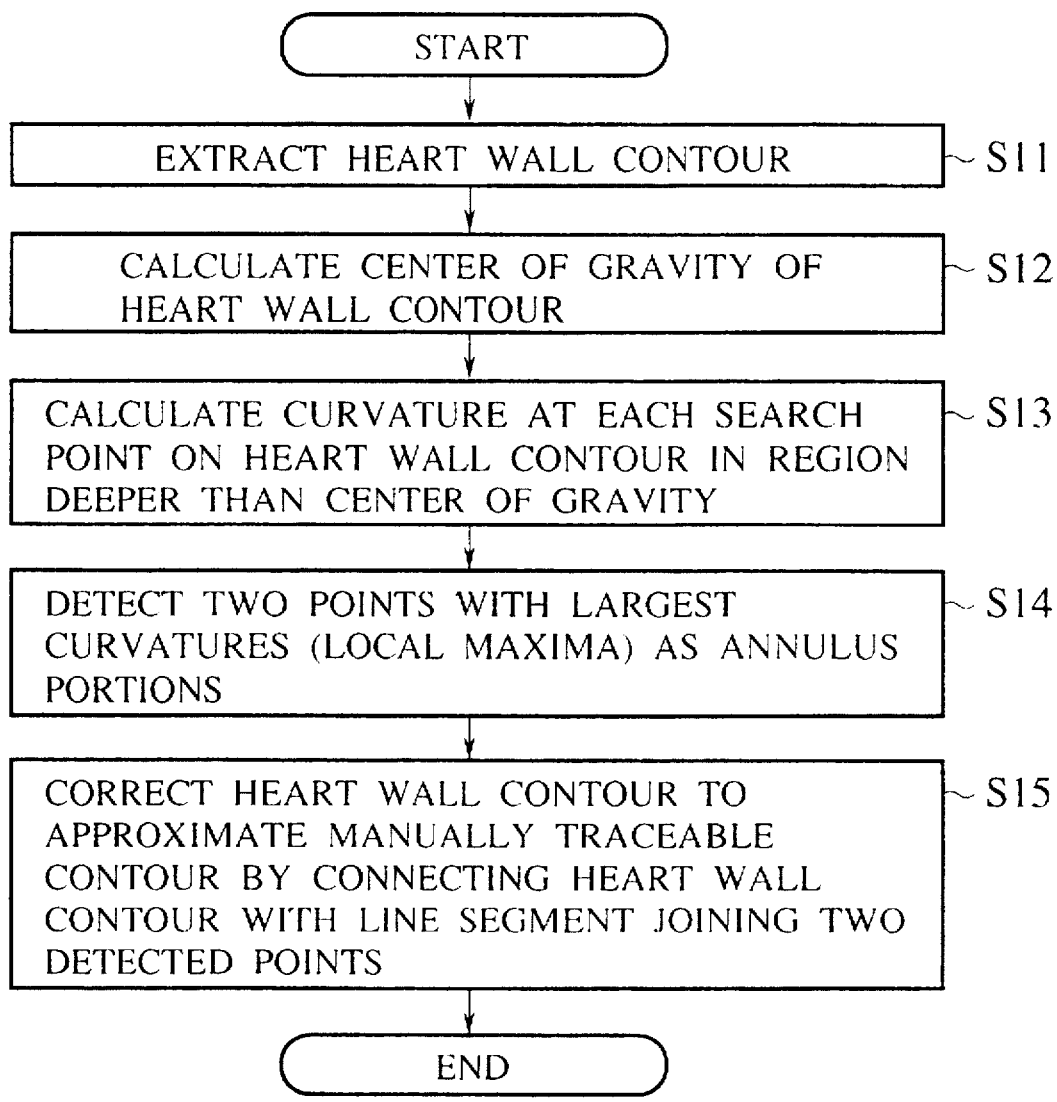
FIG. 6 Is a flow chart for the operation of the ultrasonic image processing apparatus of FIG. 5 in a first mode.
Figure 7:
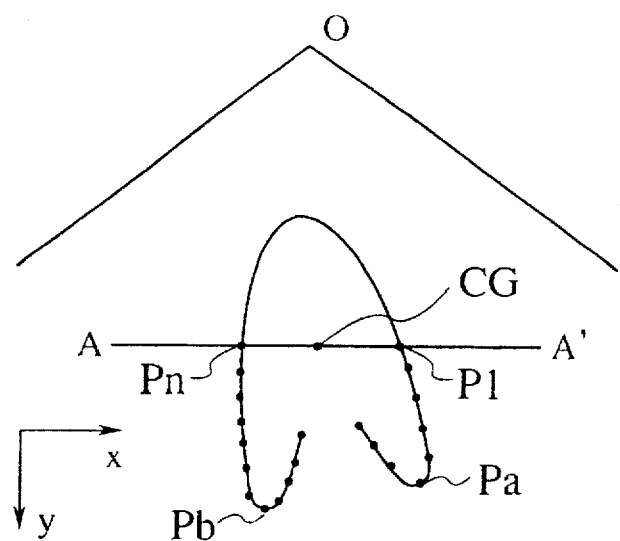
FIG. 7 is an illustration of a heart wall contour in a course of the operation of FIG. 6.

The processing procedure in this first mode is shown in the flow chart of FIG. 6, and the heart wall contour extracted by the heart wall contour extraction unit 5 in this first mode is shown in FIG. 7. Note that a point 0 shown in FIG. 7 is a position corresponding to the ultrasonic probe (a transmission/reception position) on the ultrasonic image.

First, the heart wall contour is extracted from the ultrasonic image by the heart wall contour extraction unit 5 according to the automatic tracing method of FIG. 3B (step S11). Then, a center of gravity CG of the heart wall contour extracted by the heart wall contour extraction unit 5 is calculated by the annulus portion detection unit 6 (step S12).

Next, a plurality of search points P1 to Pn are set up on a part of the heart wall contour in a region deeper than the center of gravity CG (a region below a line A–A' in FIG. 7), and a curvature of the heart wall contour at a position of each search point Pi is calculated by the annulus portion detection unit 6 (step S13). On the ultrasonic image, the depth direction corresponds to the y-axis direction as indicated in FIG. 7, so that a region deeper than the center of gravity CG can be recognized as a region where a y-coordinate value is greater than a y-coordinate value of the center of gravity CG. Here, all the picture elements on the heart wall contour in a region deeper than the center of gravity CG may be set as the search points P1 to Pn, or a relatively small number of picture elements which are discretely selected from all the picture elements may be set as the search points P1 to Pn.

Figure 8:
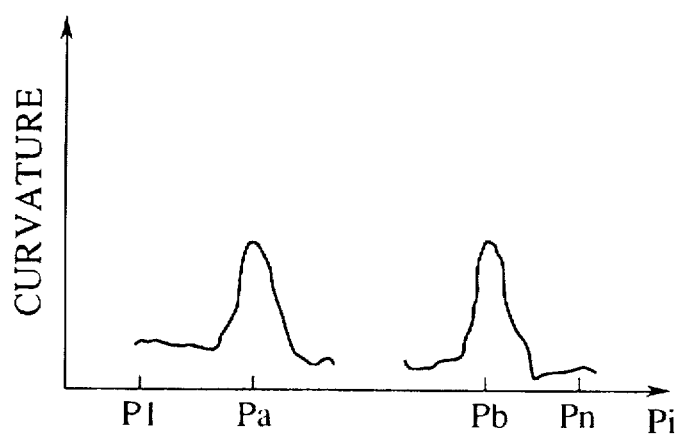
FIG. 8 is a graph of curvatures for a plurality of search points shown in FIG. 7, which is used in a course of the operation of FIG. 6.

Then, two search points Pa and Pb with two largest curvature values, or which are local maxima in a graph of curvatures for the search points P1 to Pa, are detected as the annulus portions by the annulus portion detection unit 6 (step S14). FIG. 8 shows a graph of curvatures for a plurality of search points P1 to Pn as shown in FIG. 7, where two points Pa and Pb are points of two largest curvatures as well as the local maxima in the graph of curvatures.

As already mentioned above, the annulus portion is always located at a position deeper than the apex portion on the ultrasonic image of a long axis view of the heart imaged from the apex portion side. In the heart wall contour, portions which can have large curvature values are the annulus portion and the apex portion. If a point of the largest curvature or the local maximum in a graph of curvatures is searched over an entire heart wall contour, there would be a possibility for erroneously detecting the apex portion instead of the annulus portion.

However, in this first mode, the annulus portions are searched according to the curvatures of only those points on the heart wall contour which are located deeper than the center of gravity of the heart wall contour, so that a possibility for erroneously detecting the apex portion instead of the annulus portion is eliminated, and therefore the annulus portions can be detected very accurately.

Figure 9:
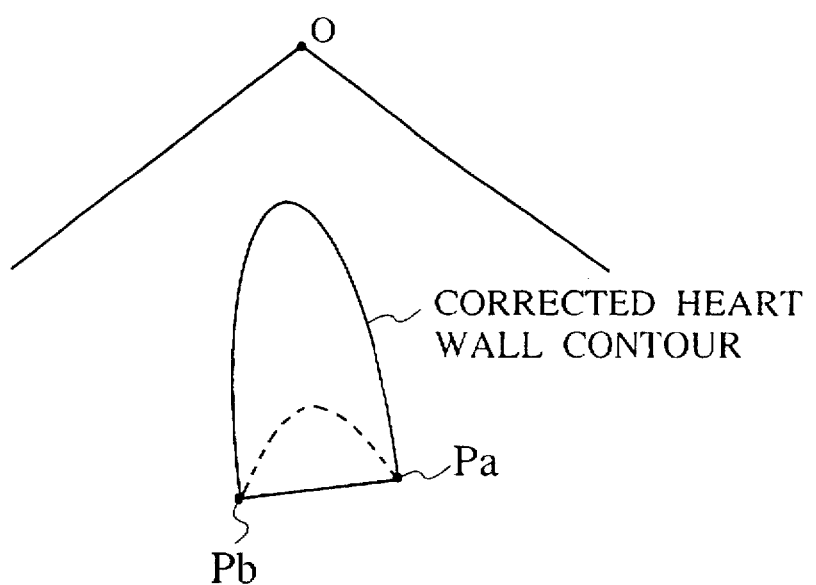
FIG. 9 is an illustration of an exemplary corrected heart wall contour obtained by the ultrasonic image processing apparatus of FIG. 5.

Finally, as shown in FIG. 9, the heart wall contour extracted by the heart wall contour extraction unit 5 is corrected to approximate a manually traceable contour (the heart wall contour obtainable in the manual tracing method) by the heart wall contour correction un it 7, by connecting the extracted heart wall contour with a straight line segment joining two annulus portions Pa and Pb detected by the annulus portion detection unit 6 (step S15).

Second mode

The second mode can deal with both the heart wall contour obtained by the automatic tracing method in which two tip ends of the mitral valve are not joined and the heart wall contour obtained by the semi-automatic tracing method in which two tip ends of the mitral valve are joined. Note that the first mode, which detects the points of the largest curvature as the annulus portions, is limited to deal only with the heart wall contour obtained by the automatic tracing method in which two tip ends of the mitral valve are not joined because, in a case of the heart wall contour obtained by the semi-automatic tracing method in which two tip ends of the mitral valve are joined, a portion connecting between two tip ends of the mitral valve can have a large curvature so that there is a possibility for erroneously detecting this point instead of the annulus portions.

Figure 10:
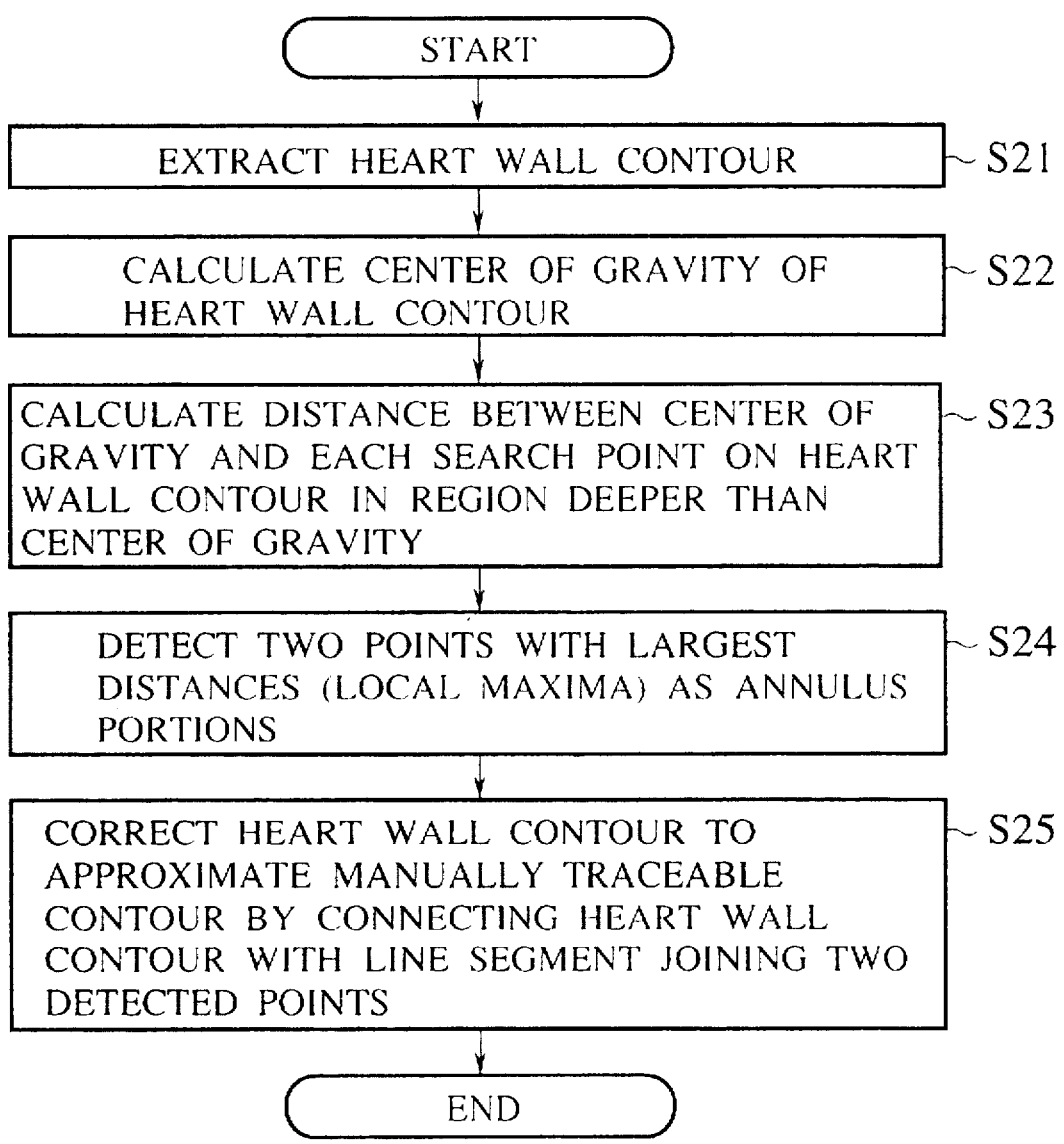
FIG. 10 is a flow chart for the operation of the ultrasonic image processing apparatus of FIG. 5 in a second mode.
Figure 11:
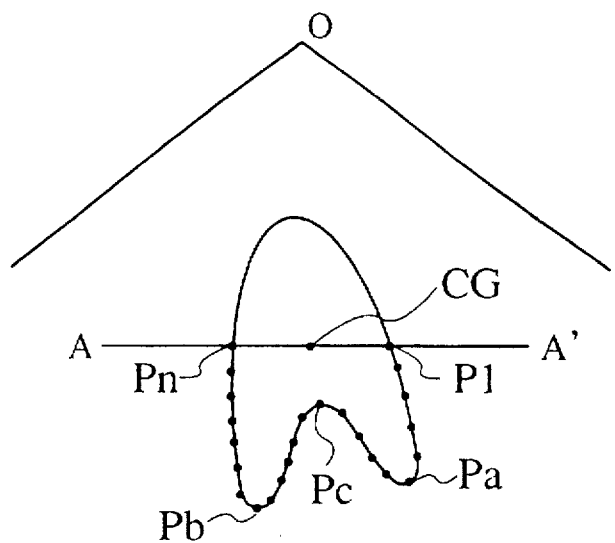
FIG. 11 is an illustration of a heart wall contour in a course of the operation of FIG. 10.

The processing procedure in this second mode is shown in the flow chart of FIG. 10, and the heart wall contour extracted by the heart wall contour extraction unit 5 in this second mode is shown in FIG. 11.

First, the heart wall contour is extracted from the ultrasonic image by the heart wall contour extraction unit 5 according to the automatic tracing method of FIG. 3B or the semi-automatic tracing method of FIG. 3C (step S21). Then, a center of gravity CG of the heart wall contour extracted by the heart wall contour extraction unit 5 is calculated by the annulus portion detection unit 6 (step S22).

Next, a plurality of search points P1 to Pn are set up on a part of the heart wall contour in a region deeper than the center of gravity CG (a region below a line A–A' in FIG. 11), and a distance between the center of gravity CG and each search point Pi is calculated by the annulus portion detection unit 6 (step S23). Here, the distance L can be calculated by the following formula (1):

$$Li = \{(Ci(x)-G(x))^2 + (ci(y)-G(y))^2\}^{1/2} \quad (1)$$

where $Ci(x)$ is an x-coordinate value on the image data of the i-th search point Pi, $Ci(y)$ is a y-coordinate value on the image data of the i-th search point Pi, $G(x)$ is an x-coordinate value on the image data of the center of gravity CG, $G(y)$ is a y-coordinate value on the image data of the center of gravity CG, and $1 \leq i \leq n$. Here, similarly as in the first mode, all the picture elements on the heart wall contour in a region deeper than the center of gravity CG may be set as the search points P1 to Pn, or a relatively small number of picture elements which are discretely selected from all the picture elements may be set as the search points P1 to Pn.

Figure 12:
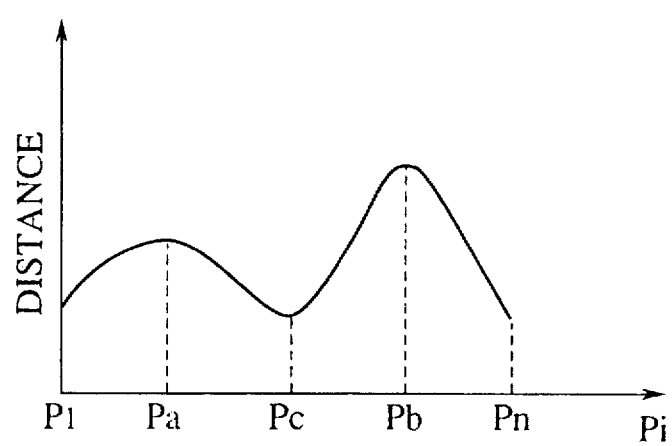
FIG. 12 is a graph of distances for a plurality of search points shown in FIG. 11, which is used in a course of the operation of FIG. 10.

Then, two search points Pa and Pb with two largest distance values, or which are local maxima in a graph of distances for the search points P1 to Pn, are detected as the annulus portions by the annulus portion detection unit 6 (step S24). FIG. 12 shows a graph of distances for a plurality of search points P1 to Pn as shown in FIG. 11, where two points Pa and Pb are points of two largest distances as well as the local maxima in the graph of distances.

As already mentioned above, the annulus portion is always located at a position deeper than the apex portion on the ultrasonic image of a long axis view of the heart imaged from the apex portion side. In the ultrasonic image of a long axis view, portions which can have large distances with respect to the center of gravity CG of the heart wall contour are the annulus portion and the apex portion. If a point of the largest distance or the local maximum in a graph of distances is searched over an entire heart wall contour, there would be a possibility for erroneously detecting the apex portion instead of the annulus portion.

However, in this second mode, the annulus portions are searched according to the distances with respect to the center of gravity of only those points on the heart wall contour which are located deeper than the center of gravity of the heart wall contour, so that a possibility for erroneously detecting the apex portion instead of the annulus portion is eliminated, and therefore the annulus portions can be detected very accurately.

Finally, as shown in FIG. 9, the heart wall contour extracted by the heart wall contour extraction unit 5 is corrected to approximate a manually traceable contour (the heart wall contour obtainable in the manual tracing method) by the heart wall contour correction unit 7, by connecting the extracted heart wall contour with a straight line segment joining two annulus portions Pa and Pb detected by the annulus portion detection unit 6 (step S25).

Note that the annulus portions are detected in the second mode described above by dealing only with the points on the heart wall contour which are located deeper than the center of gravity of the extracted heart wall contour, viewing from the ultrasonic probe along the depth direction, but it is also possible to modify this second mode to use the apex portion instead of the center of gravity CG as a reference point of the distance calculation.

Third mode

The third mode approximates the heart wall contour obtained by the automatic tracing method or the semi-automatic tracing method by a triangle, and detects the annulus portions from this triangle.

The processing procedure in this third mode is shown in the flow chart of FIG. 13.

First, the heart wall contour is extracted from the ultrasonic image by the heart wall contour extraction unit 5 according to the automatic tracing method of FIG. 3B or the semi-automatic tracing method of FIG. 3C (step S31). Then, the heart wall contour extracted by the heart wall contour extraction unit 5 is approximated by a triangle as shown in FIG. 14A (step S32), and a center of gravity CG of this approximating triangle is calculated by the annulus portion detection unit 6 (step S33).

Figure 14A:
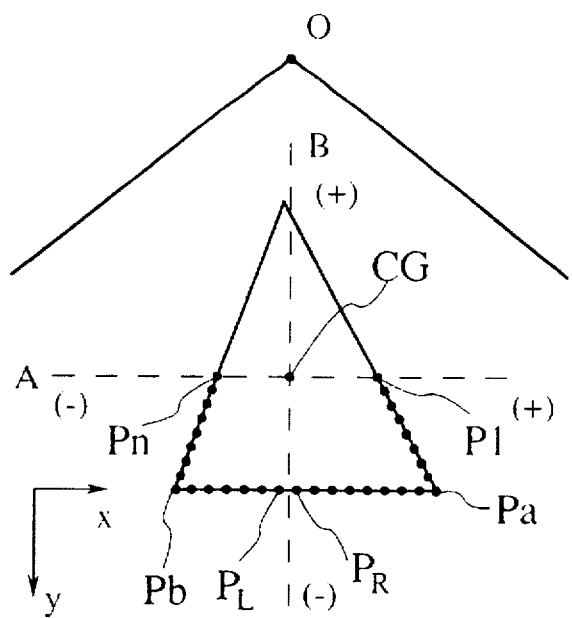
FIG. 14A is an illustration of a heart wall contour approximating triangle in a course of the operation of FIG. 13.

Next, a plurality of search points P1 to PR are set up on a part of the approximating triangle in a region deeper than and right side of the center of gravity CG (a region of (+) along a line A and (−) along a line B in FIG. 14A), and a distance between the center of gravity CG and each search point Pi is calculated by the annulus portion detection unit 6 (step S34). Here, the distance L can be calculated by the formula (1) used in the second mode. Also, similarly as in the first mode, all the picture elements on the approximating triangle in a region deeper than and right side of the center of gravity CO may be set as the search points P1 to PR, or a relatively small number of picture elements which are discretely selected from all these picture elements may be set as the search points P1 to PR.

Then, a search point Pa (first point) with the largest distance value, or which is the local maximum in a graph of distances for the search points P1 to PR, is detected as the annulus portion by the annulus portion detection unit 6 (step S35).

Next, a plurality of search points PL to Pn are set up on a part of the approximating triangle in a region deeper than and left side of the center of gravity CG (a region of (−) along a line A and (−) along a line B On FIG. 14A), and a distance between the center of gravity CC and each search point Pi is calculated by the annulus portion detection unit 6 (step S36). Here, the distance L can be calculated by the formula (1) used in the second mode. Also, similarly as in the first mode, all the picture elements on the approximating triangle in a region deeper than and left side of the center of gravity CG may be set as the search points PL to Pn, or a relatively small number of picture elements which are discretely selected from all these picture elements may be set as the search points PL to Pn.

Then, a search point Pb (second point) with the largest distance value, or which is the local maximum in a graph of distances for the search points PL to Pn, is detected as the annulus portion by the annulus portion detection unit 6 (step S37).

Figure 14B:
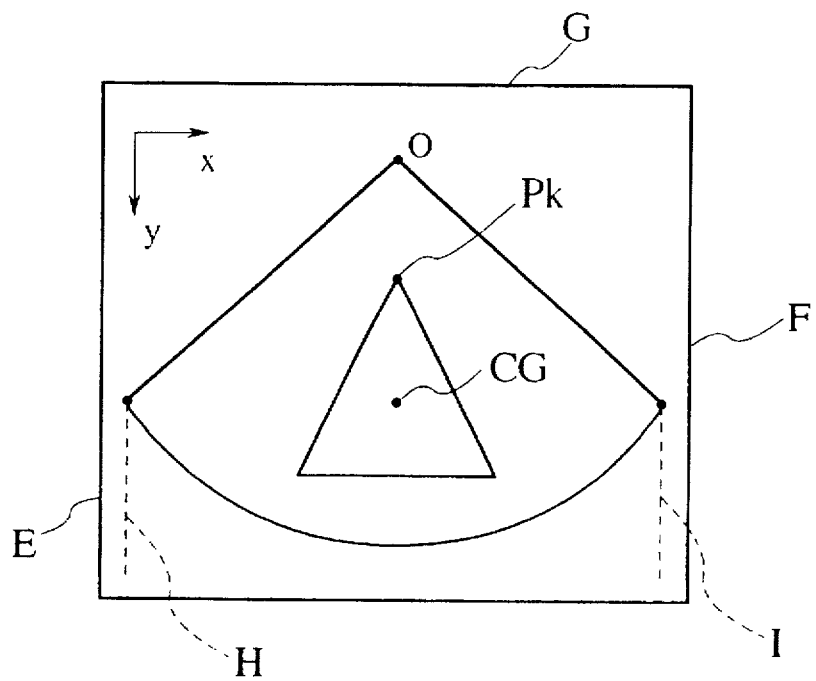
FIG. 14B is an illustration of a heart wall contour approximating triangle used in the operation of FIG. 13, in relation to-an ultrasonic beam scanning range and a display screen.

Note that the reference point of the distance calculation in this third mode is not necessarily limited to the center of gravity CO, and any of the edges E, F, and G of a display screen, edges H and I of the ultrasonic beam scanning range, the ultrasonic beam transmission/reception position O, and the apex portion Pk shown in FIG. 14B can be used instead of the center of gravity CG.

For example, a distance Li(right) for each of the search points P1 to PR on the approximating triangle in a region deeper than and right side of the center of gravity CO and a distance Li(left) for each of the search points PL to Pn on the approximating triangle in a region deeper than and left side of the center of gravity CG can be calculated by the following formula (2):

$$Li(\text{left}) = \alpha \times Yi + \beta \times 1/Xi$$

$$Li(\text{right}) = \alpha \times Yi + \beta \times Xi \quad (2)$$

where $\alpha$ and $\beta$ are weight factors, Yi is a Distance in a y-direction of the i-th search point Pi with respect to the upper edge G of the display screen or the ultrasonic beam transmission/reception position O or the center of gravity CG, and Xi is a distance in an x-direction of the i-th search point Pi with respect to the left edge E of the display screen or the left edge H of the scanning range. In this case, one search point with the largest value for Li(left) and another search point with the largest value for Li(right) will be detected as the annulus portions.

Alternatively, instead of the above formula (2), it is also possible to calculate Li(left) and Li(right) by the following formula (3):

$$Li(\text{left}) = \alpha \times Yi + \beta \times 1/Xil$$

$$Li(\text{right}) = \alpha \times Yi + \beta \times 1/Xir \quad (3)$$

where $\alpha$ and $\beta$ are weight factors, Yi is a distance in a y-direction of the i-th search point Pi with respect to the upper edge G of the display screen or the ultrasonic beam transmission/reception position O or the center of gravity CG, Xil is a distance in an x-direction of the i-th search point Pi with respect to the left edge E of the display screen or the left edge H of the scanning range, and Xir is a distance in an x-direction of the i-th search point Pi with respect to the right edge F of the display screen or the right edge I of the scanning range.

Alternatively, instead of the above formula (2), it is also possible to calculate Li(left) and Li(right) by the following formula (4):

$$Li(\text{left}) = \alpha \times Yi + \beta \times Xil'$$

$$Li(\text{right}) = \alpha \times Yi + \beta \times Xir' \quad (4)$$

where $\alpha$ and $\beta$ are weight factors, Yi is a distance in a y-direction of the i-th search point Pi with respect to the upper edge G of the display screen or the ultrasonic beam transmission/reception position O or the center of gravity CG, Xil' is a distance in an x-direction of the i-th search point Pi on left side of the center of gravity CG with respect to the center of gravity CG, and Xir' is a distance in an x-direction of the i-th search point Pi on right side of the center of gravity CG with respect to the center of gravity CG.

Finally, as shown in FIG. 9, the heart wall contour extracted by the heart wall contour extraction unit 5 is corrected to approximate a manually traceable contour (the heart wall contour obtainable in the manual tracing method) by the heart wall contour correction unit 7, by connecting the extracted heart wall contour with a straight line segment joining two annulus portions Pa and Pb (first and second points) detected by the annulus portion detection unit 6 (step S38).

Fourth mode

Figure 15A:
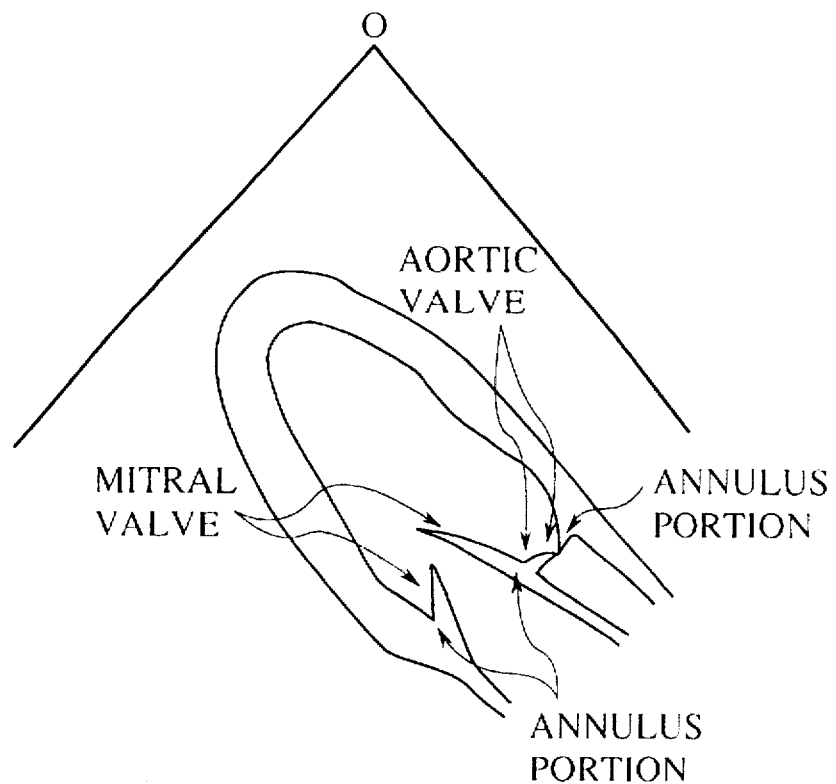
FIG. 15A is an illustration of an exemplary ultrasonic image to be handled in the operation of the ultrasonic image processing apparatus of FIG. 5 in a fourth mode.

The fourth mode is used when the tomographic image of the heart imaged from the apex portion side is largely inclined from a central line of the scanning range, and therefore the heart wall contour obtained by the automatic tracing method or the semi-automatic tracing method is also largely inclined. This type of inclined image is often encountered in a case of imaging a cross section of the heart from the apex portion side in such a manner that the aortic valve is visible in the obtained image. FIG. 15A shows an exemplary appearance of such an inclined image, while FIG. 15B shows the heart wall contour extracted from this inclined image according to the semi-automatic tracing method of FIG. 3C.

Figure 15B:
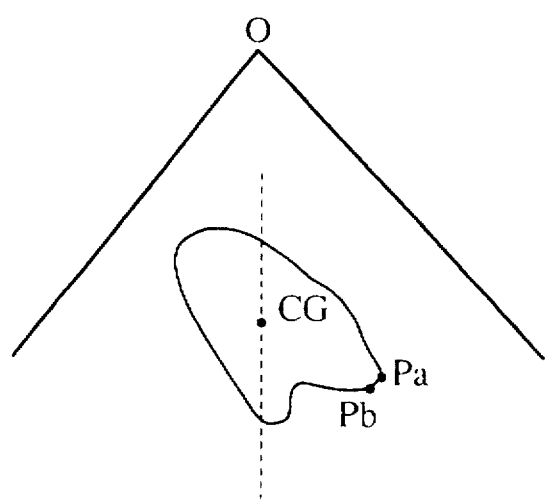
FIG. 15B is an illustration of a heart wall contour extracted from the ultrasonic image of FIG. 15A.
Figure 16A:
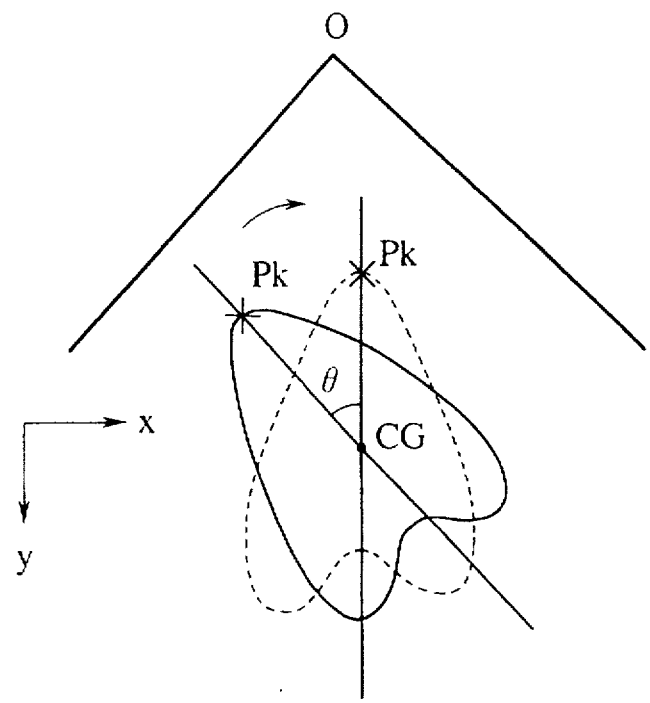
FIG. 16A is an illustration of one exemplary heart wall contour in a course of the operation of the ultrasonic image processing apparatus of FIG. 5 in a fourth mode.
Figure 16B:
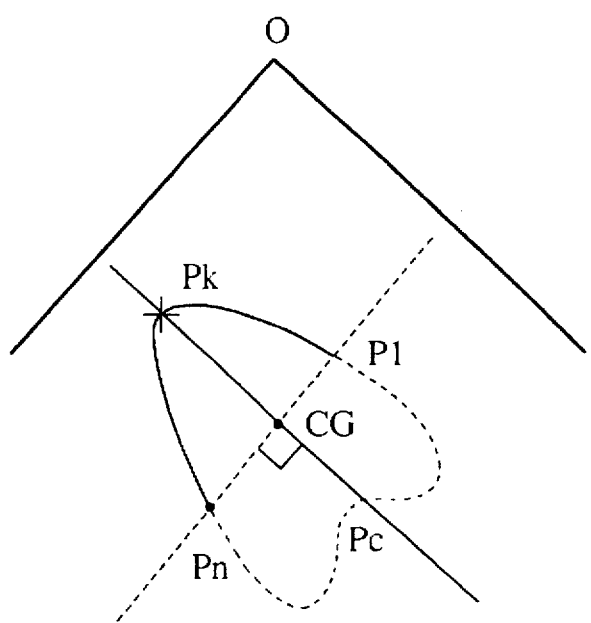
FIG. 16B is an illustration of another exemplary heart wall contour in a course of the operation of the ultrasonic image processing apparatus of FIG. 5 in a fourth mode.

In this case, if the second mode described above is used to select two points with the largest distances calculated according to the above formula (1) from the points on the heart wall contour which are located deeper than the center of gravity CG, for example, there is a possibility for detecting the annulus portions incorrectly as points Pa and Pb shown in FIG. 15B. Also, because the annulus portions are both on right side of the center of gravity CG on the image, it is impossible to detect these annulus portions automatically by dividing a region on right side of the center of gravity CG and a region on left side of the center of gravity CG as in the third mode described above. In such a case, it is still possible to detect the annulus portions correctly if the third mode is executed by utilizing the knowledge that both of the annulus portions are located on right side of the center of gravity CG, but it is preferable to use the fourth mode as described below.

In this fourth mode, the apex portion Pk is detected from the extracted heart wall contour first. Here, the apex portion Pk can be detected by setting the apex portion Pk as a point which is located at the shallowest position in the depth direction among all the extracted contour points, viewing from the ultrasonic probe (ultrasonic beam transmission/ reception position), or by setting the apex portion Pk as a point for which the distance from the center of gravity CG is the largest among all the points in a region shallower than the center of gravity CG in the depth direction. It is also possible to detect the apex portion Pk by the other method, such as a manual specification.

Figure 18A:
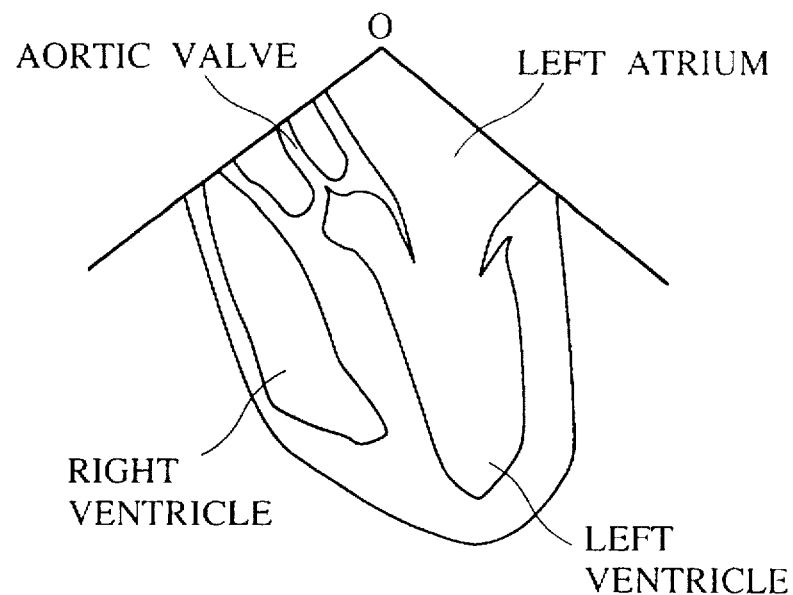
FIGS. 18A and 18B are illustrations of exemplary ultrasonic images obtained by the transesophageal echocardiography.

Next, as shown in FIG. 18A, the extracted heart wall contour is rotated with respect to the frame for an angle θ such that the straight line joining the detected apex portion Pk and the center of gravity CG becomes parallel to the y-axis (the depth direction viewed from the ultrasonic probe (ultrasonic beam transmission/reception position)). When the heart wall contour is rotated in this manner, the annulus portions are separately positioned at left and right of the center of gravity CG in a region deeper than the center of gravity CG, so that the annulus portions can be detected by subsequently using any of the first to third modes described above.

Note that, in this fourth mode, instead of rotating the extracted heart wall contour as described above, it is also possible to detect the annulus portions by dividing a part of the heart wall contour in a region farther away from the apex portion Pk than the center of gravity CG (a dashed line region shown in FIG. 16B) into a section from P1 to Pc and a section from Pc to Pn, and applying the third mode described above to these divided sections.

Also, in the above description, the extracted heart wall contour is rotated, but in a case where an inclination angle of the tomographic image of the heart can be ascertained in advance in some way, it is also possible in this fourth mode to detect the annulus portions by rotating the inclined image itself first, then extracting the heart wall contour from this rotated image according to the automatic tracing method or the semi-automatic tracing method, and subsequently using any of the first to third modes described above with respect to the extracted heart wall contour.

Fifth mode

The fifth mode is used in a case of detecting the annulus portions from the tomographic image of the heart imaged by the transesophageal echocardiography.

Figure 17:
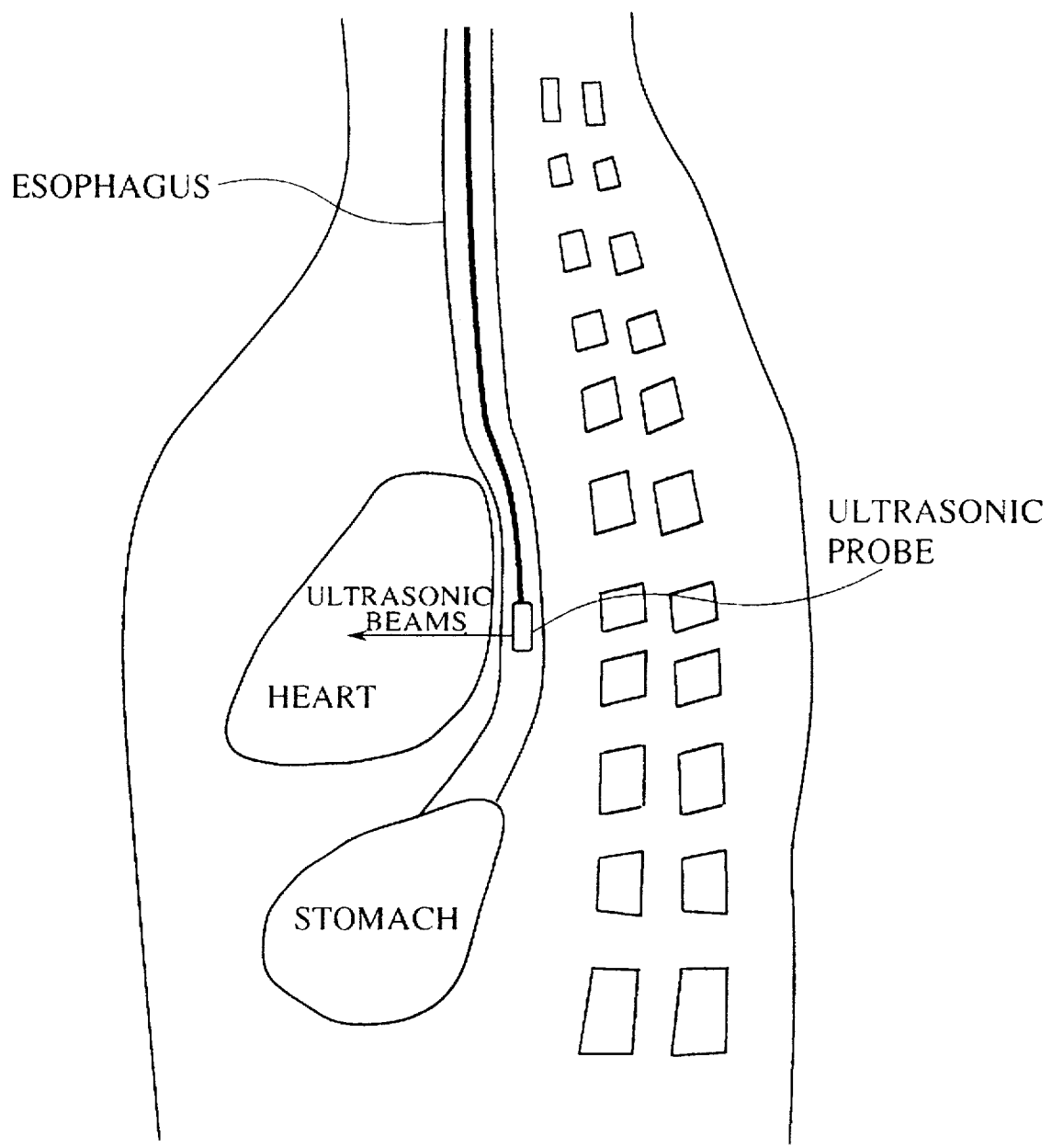
FIG. 17 is an illustration of a cross section of a human body showing a manner of obtaining a tomographic image of a heart by the transesophageal echocardiography.
Figure 18B:
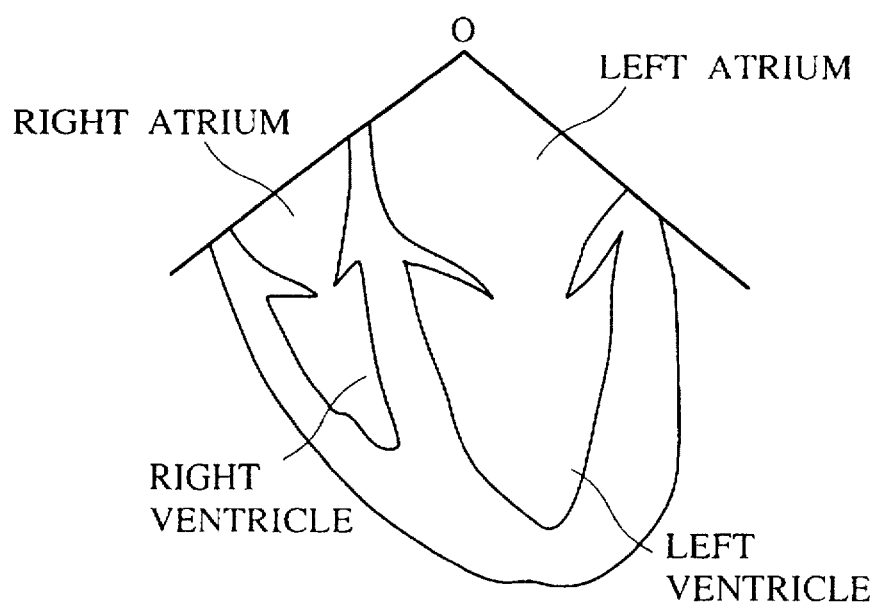
Figure 19:
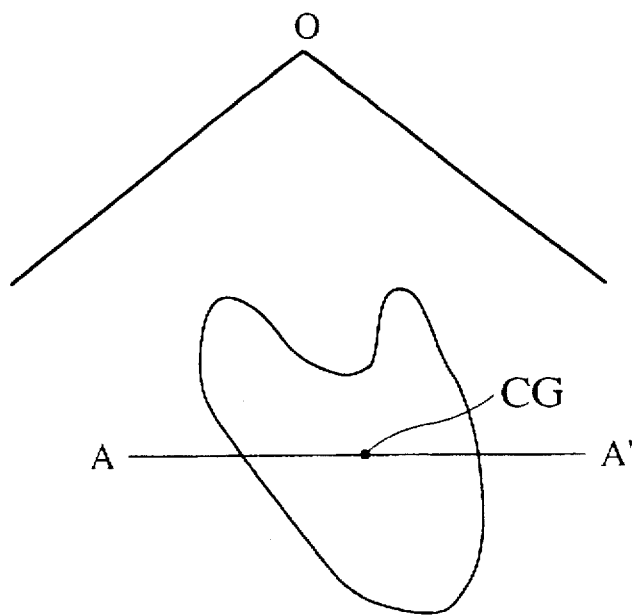
FIG. 19 is an illustration of one exemplary heart wall contour in a course of the operation of the ultrasonic image processing apparatus of FIG. 5 in a fifth mode.
Figure 20:
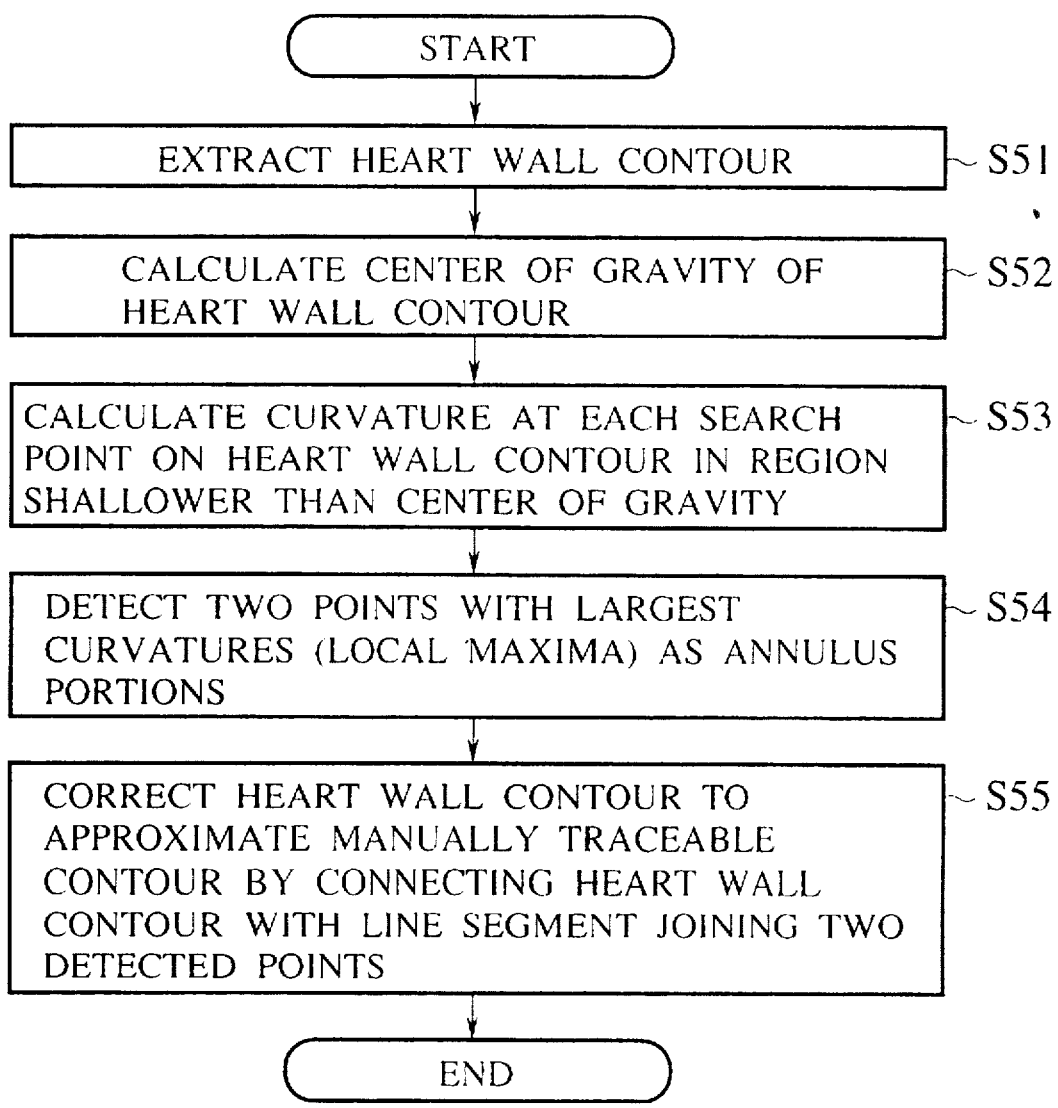
FIG. 20 is a flow chart for the operation of the ultrasonic image processing apparatus of FIG. 5 in a fifth mode.

The transesophageal echocardiography is a method for obtaining the tomographic image of the heart from inside the esophagus by inserting the ultrasonic probe into the esophagus of a body to be examined, as shown in FIG. 17. When a long axis view of the heart is imaged using this transesophageal echocardiography, the obtained image appears as shown in FIG. 18A or FIG. 18B, which is upside down of the image obtained in a case of imaging from the apex portion side such as that shown in FIG. 2. Consequently, the positional relationship between the center of gravity of the heart wall contour and the annulus portions becomes a reversal of that in the first to fourth modes described above, as shown in FIG. 19.

For this reason, in this fifth mode, the annulus portions are detected from a region shallower than the center of gravity in the extracted heart wall contour. After a region which contains the annulus portions is specified in the heart wall contour, the annulus portions can be detected in a manner similar to any of the first to third modes described above.

The processing procedure in this fifth mode in an exemplary case of utilizing a manner similar to the first mode described above is shown in the flow chart of FIG. 20.

First, the heart wall contour is extracted from the ultrasonic image by the heart wall contour extraction unit 5 according to the automatic tracing method of FIG. 3B (step S51). Then, a center of gravity CG of the heart wall contour extracted by the heart wall contour extraction unit 5 is calculated by the annulus portion detection unit 6 (step S52).

Next, a plurality of search points P1 to Pn are set up on a part of the heart wall contour in a region shallower than the center of gravity CG (a region above a line A—A' in FIG. 19), and a curvature of the heart wall contour at a position of each search point Pi is calculated by the annulus portion detection unit 6 (step S53).

Then, two search points Pa and Pb with two largest curvature values, or which are local maxima in a graph of curvatures for the search points P1 to Pn, are detected as the annulus portions by the annulus portion detection unit 6 (step S54).

Finally, as shown in FIG. 9, the heart wall contour extracted by the heart wall contour extraction unit 5 is corrected to approximate a manually traceable contour (the heart wall contour obtainable in the manual tracing method) by the heart wall contour correction unit 7, by connecting the extracted heart wall contour with a straight line segment joining two annulus portions Pa and Pb detected by the annulus portion detection unit 6 (step S55).

Figure 21:
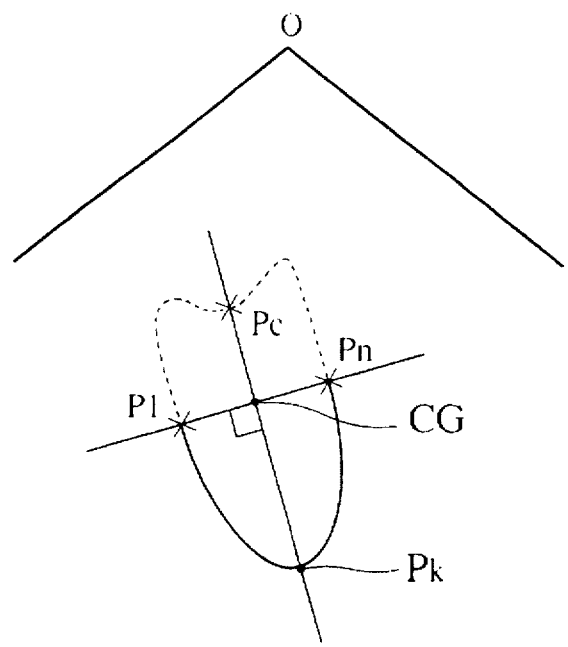
FIG. 21 is an illustration of another exemplary heart wall contour in a course of the operation of the ultrasonic image processing apparatus of FIG. 5 in a fifth mode.

It is also possible in this fifth mode to detect the annulus portions in a manner similar to that of the fourth mode described above, by detecting the apex portion Pk from the extracted heart wall contour as shown in FIG. 21. Here, the apex portion Pk can be detected by setting the apex portion Pk as a point which is located at the deepest position in the depth direction among all the extracted contour points, viewing from the ultrasonic probe (ultrasonic beam transmission/reception position), or by setting the apex portion Pk as a point for which the distance from the center of gravity CG is the largest among all the points in a region deeper than the center of gravity CG in the depth direction. It is also possible to detect the apex portion Pk by the other method, such as a manual specification.

In such a case, it is also possible to detect the annulus portions by dividing a part of the heart wall contour in a region farther away from the apex portion Pk than the center of gravity CG (a dashed line region shown in FIG. 21) into a section from P1 to Pc and a section from Pc to Pn, and applying any of the first to third modes described above to these divided sections.

Figure 22:
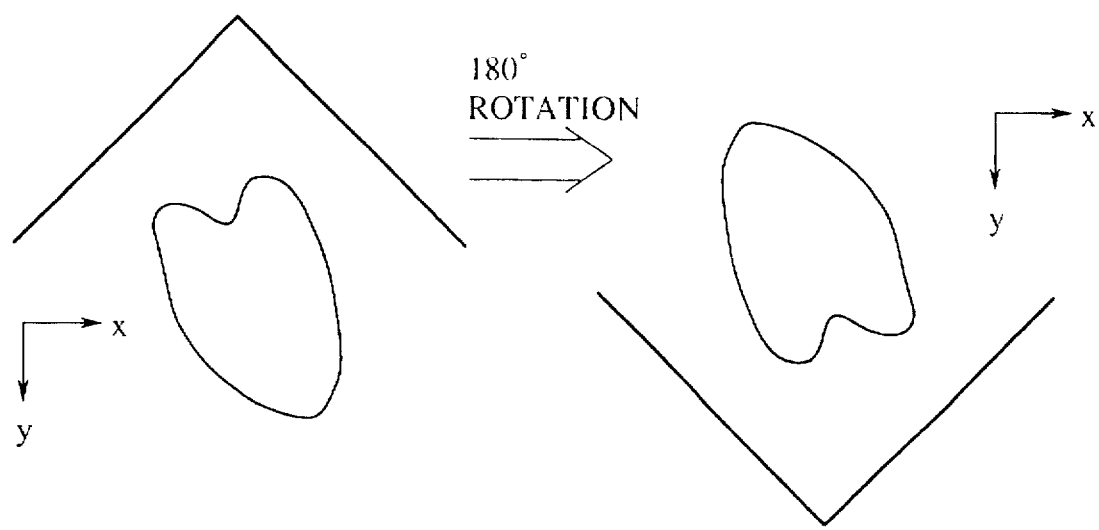
FIG. 22 is an illustration of another exemplary heart wall contour in a course of the operation of the ultrasonic image processing apparatus of FIG. 5 in a fifth mode.

Also, by accounting for the fact that the positional relationship along the vertical direction is reversed in the image obtained by the transesophageal echocardiography, it is also possible to detect the annulus portions by rotating the heart wall contour or the tomographic image of the heart for 180 degrees first as shown in FIG. 22, so as to reverse the positional relationship along the vertical direction to the normal one, and subsequently using any of the first to fourth modes described above. In this case, for a depth along the depth direction, a depth with respect to the upper edge of the image (along the y-direction shown in FIG. 22) should be used rather than a depth with respect to the position of the ultrasonic probe.

Now, the processing for the cardiac function measurement in the ultrasonic image processing apparatus of FIG. 5 will be described.

Figure 23:
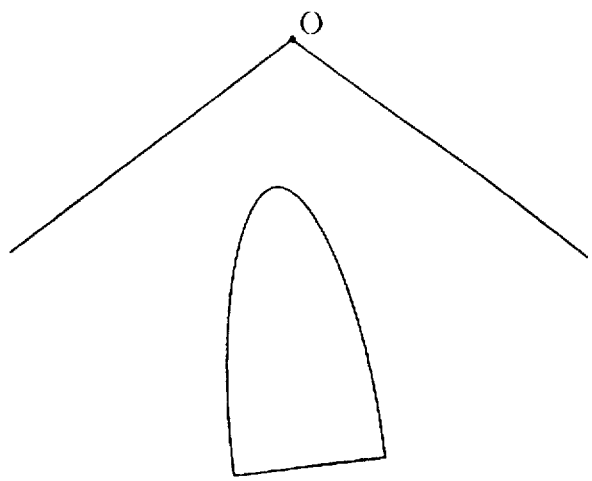
FIG. 23 is an illustration of an exemplary corrected heart wall contour used in a cardiac function measurement processing by the ultrasonic image processing apparatus of FIG. 5.

The ultrasonic image, the extracted heart wall contour, the detected annulus portions, and the corrected heart wall contour are displayed at the display unit 9 according to need. For example, FIG. 23 shows a display of the corrected heart wall contour. By suitably displaying the extracted heart wall contour, the detected annulus portions, and the corrected heart wall contour in this manner at appropriate timing, it is possible to eliminate any anxiety on the operator side, while it also becomes possible to easily judge any error in the extraction result, the detection result, or the correction result, so that it becomes possible to allow the operator to enter corrections manually or switch the operation mode to another mode when an error is found.

Then, according to the corrected heart wall contour, the cardiac function measurement unit 8 measures the cardiac function such as a heart pumping function or a local wall motion according to an area, a volume, and their changes.

For example, the area measurement can be made by dividing the corrected heart wall contour at several discrete points, making a polygonal approximation using a polygon formed by these discrete points, and calculating an area of this polygon. The area measurement can also be made by counting a number of picture elements within the corrected heart wall contour and multiplying the counted number by a real scale area size corresponding to one picture element.

Figure 24:
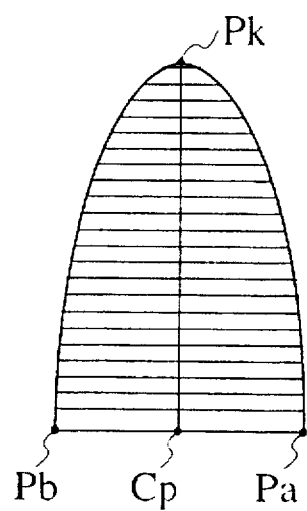
FIG. 24 is an illustration of an exemplary heart wall contour in a course of cardiac function measurement processing by the ultrasonic image processing apparatus of FIG. 5.

As for the volume measurement, as shown in FIG. 24, a straight line (major axis line) between the apex portion Pk and a central point Cp of the annulus portions Pa and Pb is drawn, and a plurality of cross sections perpendicular to that major axis line are set up. Then, a volume of a column obtained by rotating each cross section around the major axis line is added up to give a volume V of the cardiac pool. More specifically, this volume V can be calculated according to the following formula (5):

$$V = La/N \times \pi \times \Sigma_j(r_j^2) \tag{5}$$

where La is a length of the major axis line, $r_j$ is a radius of the j-th cross section, and N is a number of cross sections.

Note that the apex portion Pk can be detected from the corrected heart wall contour as a point closest to the ultrasonic beam transmission/reception position 0 (a shallowest point) on the heart wall contour, or as a point with the largest curvature value in a region closer to the ultrasonic transmission/reception position 0 (a shallower region) than the center of gravity CG in the corrected heart wall contour. The apex portion Pk may be detected by any other suitable method.

Figure 25:
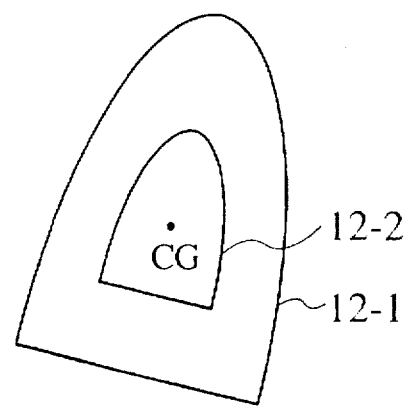
FIG. 25 is an illustration of exemplary heart wall contours in a course of local wall motion measurement processing by the ultrasonic image processing apparatus of FIG. 5.
Figure 26:
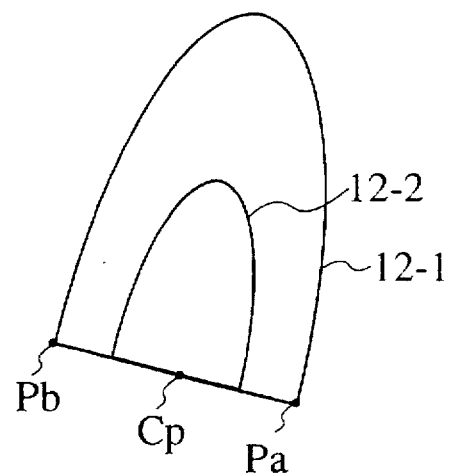
FIG. 26 is an illustration of other exemplary heart wall contours in a course of local wall motion measurement processing by the ultrasonic image processing apparatus of FIG. 5.
Figure 27:
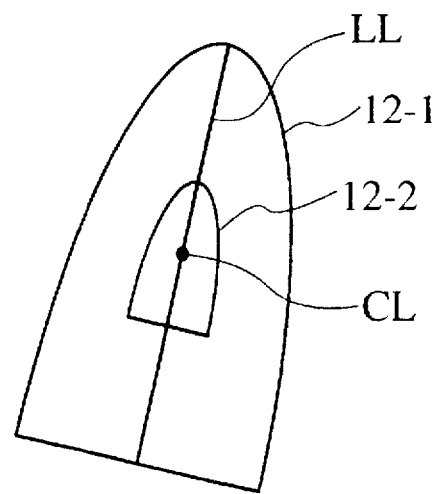
FIG. 27 is an illustration of other exemplary heart wall contours in a course of local wall motion measurement processing by the ultrasonic image processing apparatus of FIG. 5.

As for the local wall motion measurement, the heart wall contours obtained at the systolic phase and the diastolic phase are superposed with a position alignment as shown in FIG. 25 to FIG. 27, and the wall motion is measured by using the analysis method such as the center-line method. FIG. 25 shows an exemplary case in which the heart wall contour 12-1 obtained at the diastolic phase and the heart wall contour 12-2 obtained at the systolic phase are superposed with a position alignment to set their centers of gravity CG at an identical position. FIG. 26 shows an exemplary case in which the heart wall contour 12-1 obtained at the diastolic phase and the heart wall contour 12-2 obtained at the systolic phase are superposed with a position alignment to overlap their straight line segments joining the annulus portions Pa and Pb while setting central points Cp of these straight line segments at an identical position. FIG. 27 shows an exemplary case in which the heart wall contour 12-1 obtained at the diastolic phase and the heart wall contour 12-2 obtained at the systolic phase are superposed with a position alignment to overlap their major axis lines LL while setting central points CL of these major axis lines LL at an identical position.

The cardiac function information measured in this manner is then displayed at the display unit 9. At this point, in order to eliminate any anxiety on the operator side, it is also possible to display an image of a processing in progress such as those of FIG. 24 to FIG. 27 at each stage of the processing according to the need at appropriate timing.

It is to be noted that, in the first embodiment described above, only the detected annulus portions and the heart wall contour are displayed at a time of the cardiac function measurement, but it is also possible to display the original ultrasonic image in superposition according to need.

Also, in the first embodiment described above, the area and the volume are used for the pumping function calculation in the cardiac function measurement, but it is also possible to measure the pumping function according to the blood stream. Here, a case of measuring the blood stream flowing into the left ventricle according to the information on the detected annulus portions will be described.

Figure 28:
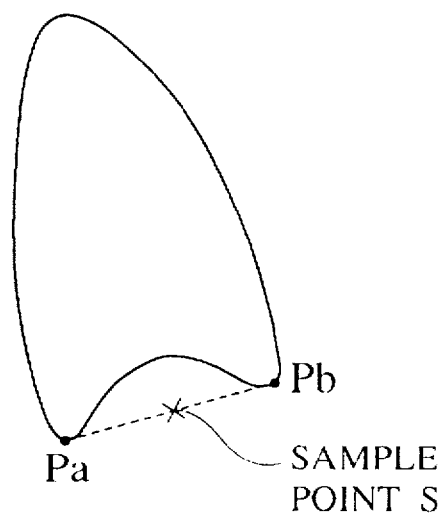
FIG. 28 is an illustration of one exemplary heart wall contour in a course of blood stream measurement processing by the ultrasonic image processing apparatus of FIG. 5.
Figure 29:
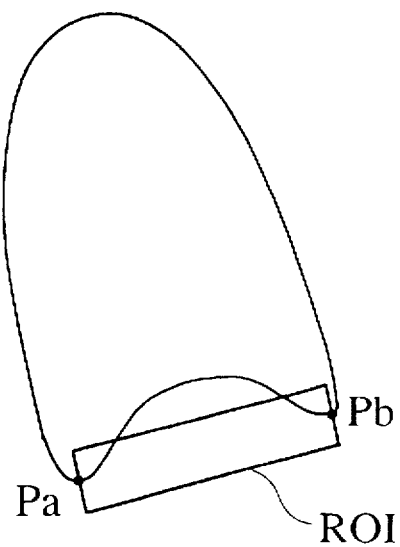
FIG. 29 is an illustration of another exemplary heart wall contour in a course of blood stream measurement processing by the ultrasonic image processing apparatus of FIG. 5.

FIG. 28 and FIG. 29 show the heart wall contour extracted by the semi-automatic tracing method of FIG. 3C and the annulus portions Pa and Pb detected according to this first embodiment.

Figure 30:
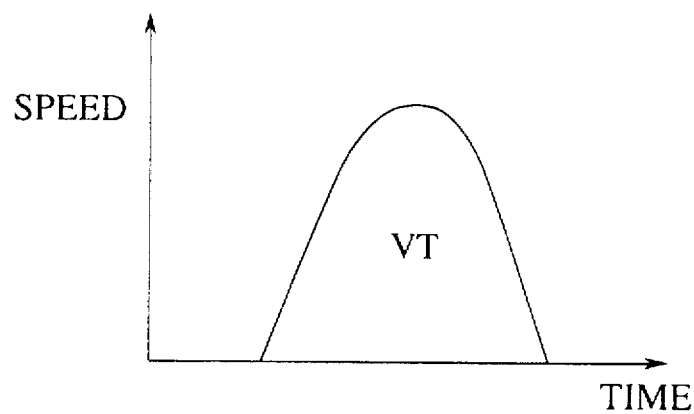
FIG. 30 is a graph of a flow speed waveform used in a course of blood stream measurement processing by the ultrasonic image processing apparatus of FIG. 5.

In FIG. 28, a sample point S (also called a sample volume) is set up at a middle point between the annulus portions Pa and Pb. Then, the flow speed waveform at the sample point S is obtained by using the pulse doppler methods and the flow speed waveform for one diastolic phase part is traced as shown in FIG. 30 either manually or automatically. Here, an area VT of an interior of the traced waveform gives an average flow speed in time.

On the other hand, by setting a length between the detected annulus portions Pa and Pb as a flow passage diameter L, the flow passage area A is calculated according to the following formula (6):

$$A = \pi \times (L/2)^2 \tag{6}$$

Then, the blood stream V flowing into the left ventricle is obtained from this flow passage area A and the average flow speed VT according to the following formula (7):

$$V = VT \times A \tag{7}$$

Thus, by obtaining this blood stream V, the diastolic function which is one of the pumping function of the heart can be measured.

Figure 31:
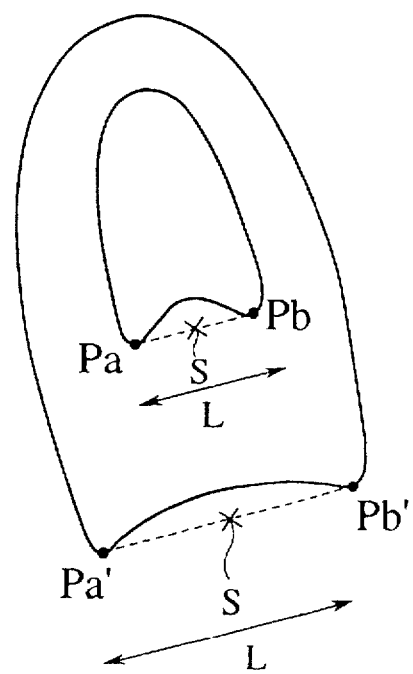
FIG. 31 is an illustration of exemplary heart wall contours in a course of blood stream measurement processing by the ultrasonic image processing apparatus of FIG. 5.

In this blood stream measurement, the setting of the sample point S and the measurement of the flow passage diameter may be made just once at a particular moment in the cardiac cycle, but as shown in FIG. 31, the sample point S and the flow passage diameter L may be changed (S→S', L→L') according to the motion of the annulus portions (Pa→Pa', Pb→Pb') so as to carry out more accurate blood stream measurement compared with a case of using a fixed sample point S.

FIG. 29 shows a case of setting up a region of interest (ROI) in a vicinity of the flow passage and calculating the blood stream according to a speed profile inside the ROI, as disclosed in Japanese Patent Application Laid-Open No. 62-26051 (1987). In this case, the ROI is set up at positions of the detected annulus portions. Then, the speed profiles inside the ROI are measured during a period of one diastolic phase, and the blood stream is measured by adding up the measured speed profiles inside the ROI.

As in a case of FIG. 28 described above, the setting of the ROI may be made just once at a particular moment in the cardiac cycle, or for more than once in conjunction with the detection of the annulus portions during the cardiac cycle. By changing the ROI according to the motion of the annulus portions, it becomes possible to carry out more accurate blood stream measurement compared with a case of using a fixed ROI.

It is to be noted that, in the above description, the sample point is set at a middle point of the annulus portions and the ROI is set at positions of the annulus portions, but the present invention is not limited to these setting schemes, and it is also possible to use any other setting schemes using the position information of the annulus portions.

Also, in the first embodiment described above, a method for detecting the annulus portions from the heart wall contour obtained by the automatic or semi-automatic tracing method is described, but the present invention is also applicable to a case using the manual tracing method in which the starting and ending points are not specified at the annulus portions, or the information on the specified starting and ending points is lost so that it is not known where the annulus portions are.

Also, the first embodiment described above may be modified by omitting the heart wall contour extraction unit 5 such that the ultrasonic image processing apparatus of the present invention receives and processes the images showing the heart wall contours already extracted by the other processing apparatus. In this case the images showing the already extracted heart wall contours are to be stored in the image memory unit 3.

Also, in the first embodiment described above, a case of processing two-dimensional ultrasonic images is described, but the present invention is similarly applicable to the three-dimensional ultrasonic images. In such a case, the heart wall contour obtained by the automatic tracing method appears as shown in FIG. 32. In this three dimensional heart wall contour, the annulus portion is detected from a region for which a spatial distance in the depth direction from the ultrasonic probe is deeper than the center of gravity CG of this heart wall contour. FIG. 33A shows an exemplary circular shape of the annulus portion detected from the three-dimensional ultrasonic image, while FIG. 33I shows an exemplary circular disk obtained by painting out an interior of the circular shape of FIG. 33A.

In this case, the annulus portion is given by a circular shaped body as shown in FIG. 33A which has three-dimensional coordinates rather than points. Then, an approximately circular plane as shown in FIG. 33B which has the same outer circumference as that of the detected annulus portion is connected to the heart wall contour of FIG. 32 to obtain the corrected three-dimensional heart wall contour which is approximating the manually obtainable contour as shown in FIG. 34. The cardiac function measurement is carried out by using this corrected heart wall contour. A manner for displaying the result and a manner for displaying during processing can be the same as described above.

As described, according to this first embodiment, it is possible provide a method and an apparatus for ultrasonic image processing, which are capable of detecting the annulus portions at high precision, from the ultrasonic image of the long axis view of a heart.

Also, according to this first embodiment, it is possible to provide a method and an apparatus for ultrasonic image processing, which are capable of automatically obtaining the heart wall contour in a simplified form in which the annulus portions are joined by a straight line segment, similarly as in a case of the manual tracing method.

Referring now through FIG. 35 to FIG. 38, the second embodiment of the present invention will be described in detail. This second embodiment is directed to a method and an apparatus for ultrasonic imaging, which realize the sensitivity correction regarding a direction perpendicular to the ultrasonic beam on the image level.

Figure 35:
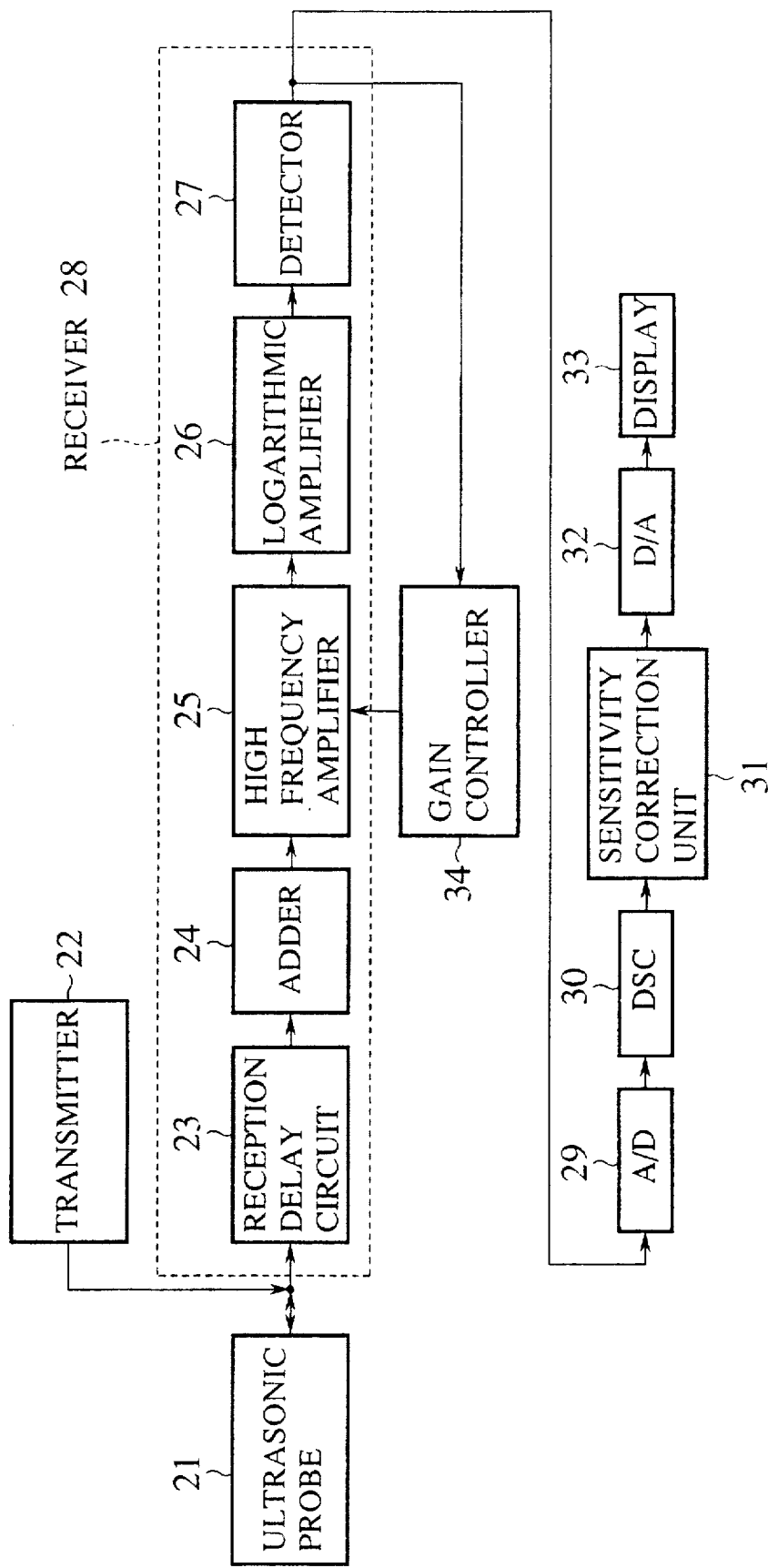
FIG. 35 is a block diagram of an ultrasonic imaging apparatus according to a second embodiment of the present invention.

An ultrasonic imaging apparatus according to this second embodiment has a configuration as shown in FIG. 35, which comprises: an ultrasonic probe 21; a transmitter 22 connected with the ultrasonic probe 21; a receiver 28 connected with the ultrasonic probe 21; a gain controller 34 connected with the receiver 28; and a series of an A/D converter 29, a digital scan converter (DSC) 30, a sensitivity correction unit 31, a D/A converter 32, and a display 33, which are connected to an output of the receiver 28.

This ultrasonic imaging apparatus of FIG. 35 is a pulse echo type apparatus using a sector electronic scanning scheme, but the present invention is also applicable to other scanning schemes such as a linear scanning scheme, a convex scanning scheme, or a mechanical scanning scheme.

The ultrasonic probe 21 is equipped with an oscillator array at its tip end, where the oscillator array has a plurality of oscillators which are arranged linearly. The high frequency pulses generated at the transmitter 22 are given to the oscillators of the oscillator array, and the ultrasonic pulses are irradiated from the ultrasonic probe 21 onto a body to be examined. The reflection beams reflected at a boundary of the acoustic impedances inside the body to be examined are received by the ultrasonic probe 21, and taken into the receiver 28 in forms of electric signals (referred hereafter as echo signals).

The receiver 28 comprises a reception delay circuit 23, an adder 24, a high frequency amplifier 25, a logarithmic amplifier 28, and a detector 27, which are connected in series, where the reception delay circuit 23 is connected with the ultrasonic probe 21, the detector 27 is connected with the gain controller 34 and the A/D converter 29, and the high frequency amplifier 25 is connected with the gain controller 34.

The reception delay circuit 23 gives different delay times to different channels of the echo signals from the ultrasonic probe 21, and the adder 24 adds up these delayed echo signals. In this manner, the echo signals in which a component in a particular direction is emphasized can be obtained. These echo signals are then amplified by the high frequency amplifier 25, and their dynamic range is changed by the logarithmic amplifier 26. Then, the detector 27 takes out the amplitude information from the echo signals in the dynamic range changed by the logarithmic amplifier 26. In the following, the signals containing this amplitude information will be referred to as the echo amplitude signals.

The gain controller 34 controls the gain of the high frequency amplifier 25 according to the echo amplitude signals outputted from the detector 27 in order to correct the inhomogeneity of the sensitivity due to the attenuation of the ultrasonic beams. Here, the gain control by this gain controller 34 raises the gain in proportion to a time elapsed since the transmission. In other words, it is the known technique of TGC (Time Gain Control) which uses a higher gain for the echo signals from a deeper portion of the body to be examined.

The echo amplitude signals outputted from the detector 27 of the receiver 28 are then converted into digital echo amplitude data by the A/D converter 29 and entered into the DSC 30. The DSC 30 carries out the scanning line conversion processing, the interpolation processing, etc. in order to convert the echo amplitude data into image data.

The image data outputted from the DSC 30 are then subjected to a sensitivity correction processing regarding a direction perpendicular to the ultrasonic beam by the sensitivity correction unit 31, as described in detail below. Then, the sensitivity corrected image data are converted into analog video signals by the D/A converter 32, and given to a display 33. The display 33 then displays the structural tomographic image (B mode image) from the received video signals.

Figure 36:
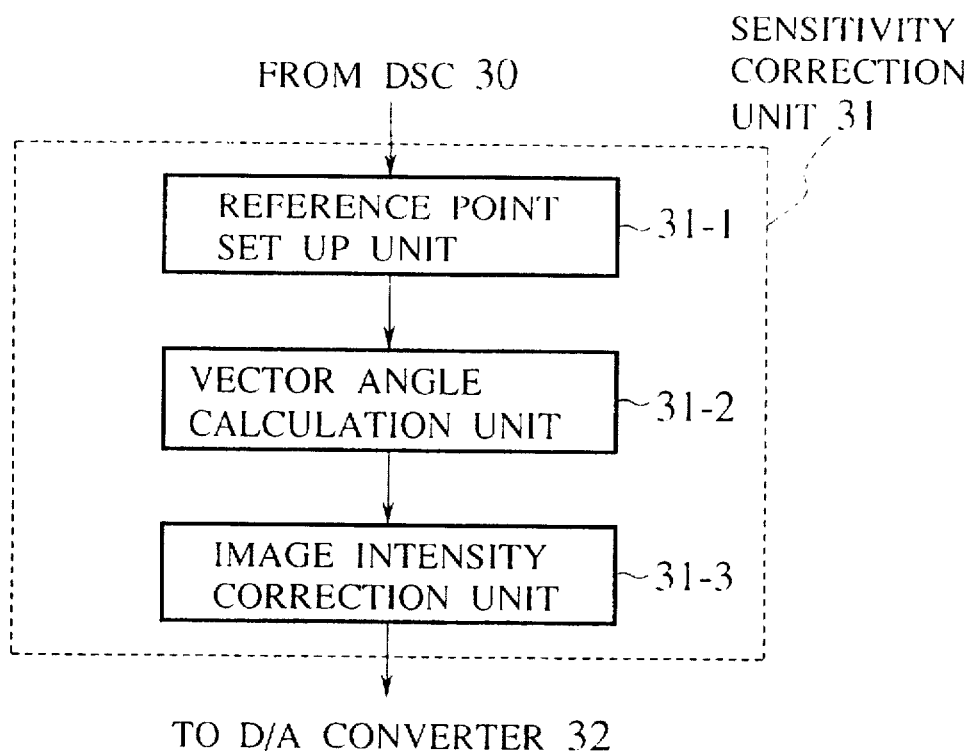
FIG. 36 is a block diagram of an internal configuration of a sensitivity correction unit in the ultrasonic imaging apparatus of FIG. 35.

The sensitivity correction unit 31 has an internal configuration as shown in FIG. 36, which comprises a reference point set up unit 31-1, a vector angle calculation unit 31-2, and an image intensity correction circuit 31-3, which are connected in series, where the reference point set up unit 31-1 is connected with the DSC 30 while the image intensity correction unit 31-3 is connected with the D/A converter 32.

The reference point set up unit 31-1 sets up a reference point such as a central point of the cardiac pool for example, within a scanning plane of the ultrasonic beams. There is no specific limitation on this reference point, so that the reference point can be a center of gravity of the heart wall contour for example, or even an arbitrary point set up by an operator.

Figure 37:
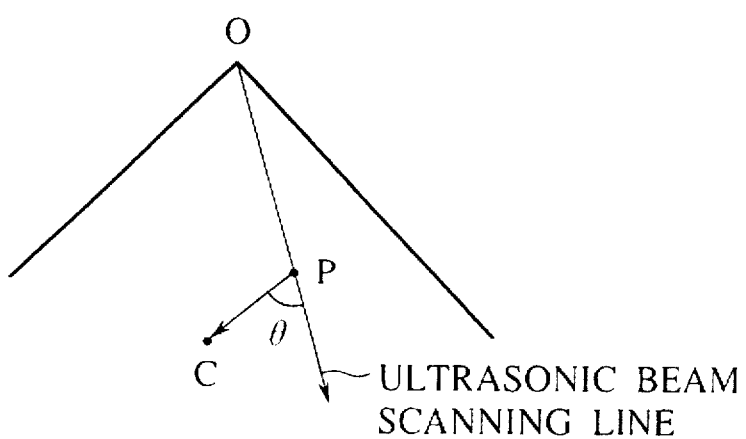
FIG. 37 is an illustration of an ultrasonic beam scanning plane showing a manner of calculating a vector angle in the ultrasonic imaging apparatus of FIG. 35.

For each one of a plurality of picture elements in the scanning plane as a target point P, the vector angle calculation unit 31-2 calculates an angle (vector angle) θ formed by a vector PC directed from the target point P to the reference point C and an ultrasonic beam (ultrasonic beam scanning line) vector OP passing through the target point P, as shown in FIG. 37.

The image intensity correction unit 31-3 makes the sensitivity correction (image intensity correction) to a picture element value (image intensity) of each picture element of the image data according to the vector angle θ of each picture element calculated by the vector angle calculation unit 31-2.

Now, the sensitivity correction in this second embodiment will be described with reference to FIG. 37 and FIG. 38. In FIG. 37, O indicates an irradiation position of the ultrasonic beam (a position of the ultrasonic probe 21), P indicates a target point, and C indicates a reference point.

First, at the vector angle calculation unit 31-2, the vector angle θ formed by a vector PC directed from the target point P to the reference point C and an ultrasonic beam (ultrasonic beam scanning line) vector OP passing through the target point P is calculated. Then, according to this vector angle θ, the image intensity correction for a picture element value of the target point P is made by the image intensity correction unit 31-3. The calculation of the vector angle θ and the image intensity correction according to the vector angle θ are carried out for each one of the picture elements in the scanning plane of the ultrasonic beams.

The image intensity correction by the image intensity correction unit 31-3 is carried out as follows.

For the target point P at coordinates (x, y), by denoting the picture element value (image intensity) of this target point P before the image intensity correction as I(x, y), and the picture element value (image intensity) of this target point P after the image intensity correction as I'(x,y), the following equation (8) holds.

$$I'(x, y) = fi(\theta, I(x, y)) \quad (8)$$

where fi(θ) is an image intensity correction function for changing the image intensity correction amount according to the vector angle θ. This image intensity correction function fi(θ) can be given by any function which has the local maximum value for θ=90° and the local minimum value for θ=0°, 180°, and which changes its value (image intensity correction strength) according to θ, as shown in FIG. 38.

For example, the above equation (8) can be rewritten as the following equation (9).

$$I'(x, y) = A \times (1 + B \times \sin(\theta)) \times I(x, y) \quad (9)$$

where A and B are constants, and 0°≦θ≦180°.

It is also possible to use the following equation (10) instead of the above equation (9).

$$I'(x, y) = A \times (1 + B \times \exp(-|\theta - 90°|)) \times I(x, y) \quad (10)$$

Figure 38:
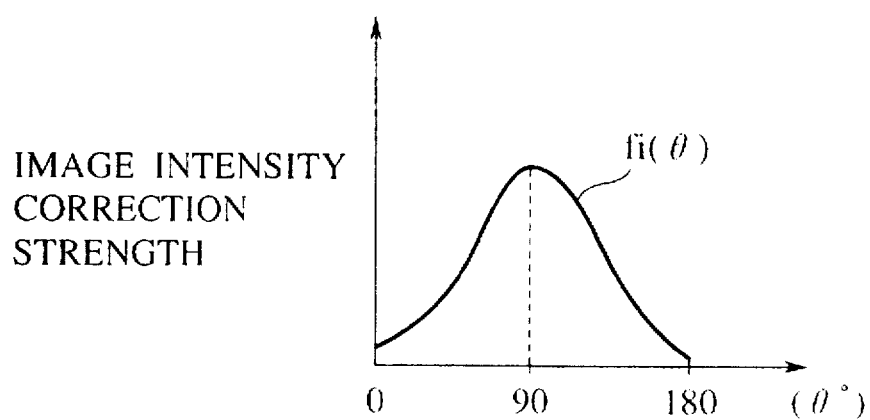
FIG. 38 is a graph showing an exemplary image intensity correction function used in the ultrasonic imaging apparatus of FIG. 35.

The image intensity correction function fi(θ) is not limited to those used in the above equations (9) and (10), and any function which changes the image intensity correction strength according to θ as shown in FIG. 38 can be used.

Moreover, in FIG. 38, the local maximum value or the local minimum value of fi(θ) may not necessarily be, constant. In other words, it is not absolutely necessary for fi(θ) to satisfy the relationship of fi(0°)=fi(180°).

Thus, according to this second embodiment, the sensitivity in a vicinity of the direction perpendicular to the ultrasonic beams (θ=90° in this embodiment) is improved. On the other hand, hardly any image intensity correction is made for portions (θ=0° and θ=180° in this embodiment) which have a good sensitivity from the beginning, so that an introduction of noise due to the excessive sensitivity correction is prevented, and it is possible to obtain the image which is easy to watch.

Referring now to FIG. 39 through FIG. 42, the third embodiment of the present invention will be described in detail. This third embodiment is directed to a method and an apparatus for ultrasonic imaging, which realize the sensitivity correction regarding a direction perpendicular to the ultrasonic beam by a gain control for the echo signals.

Figure 39:
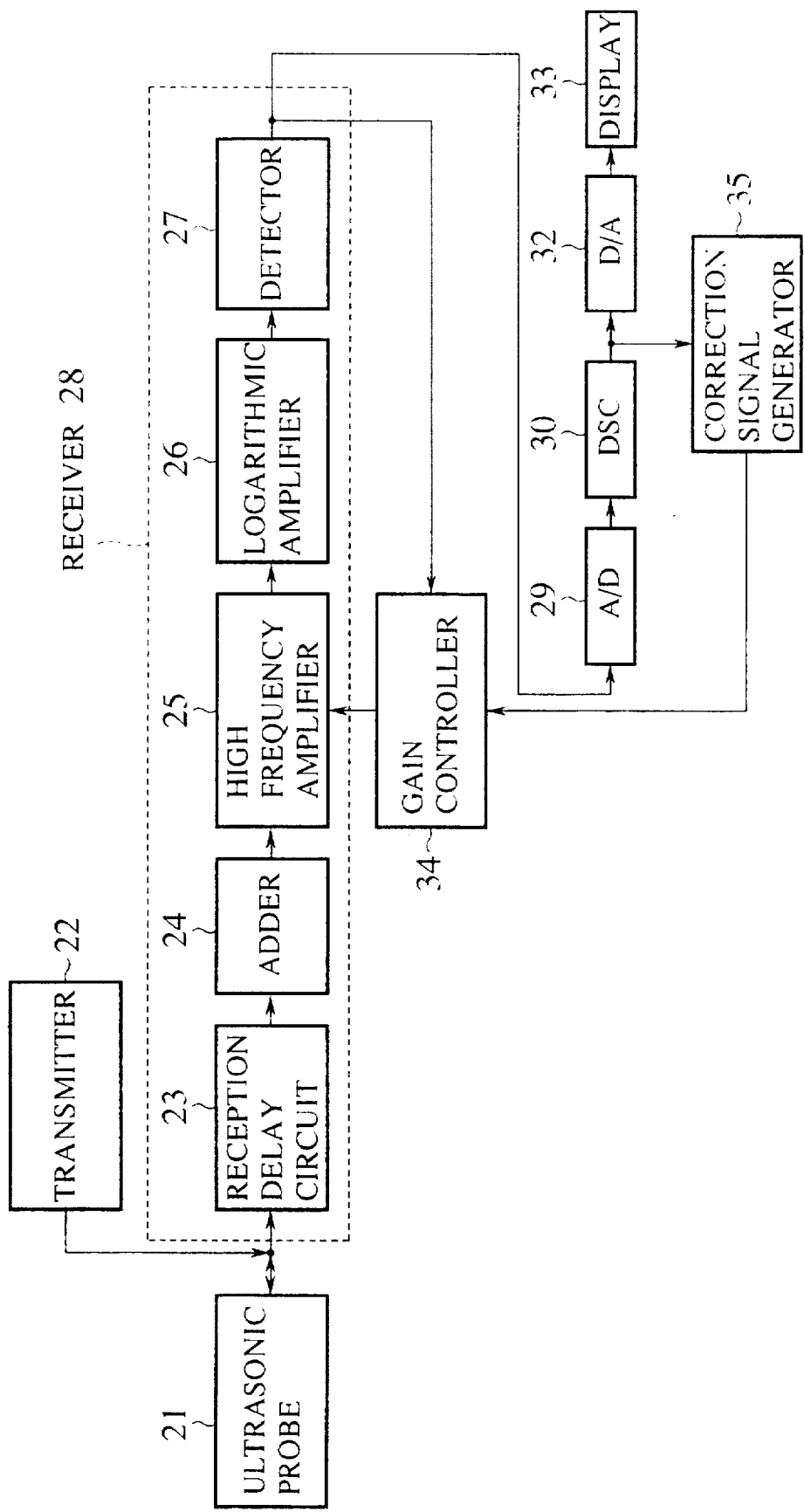
FIG. 39 is a block diagram of an ultrasonic imaging apparatus according to a third embodiment of the present invention.

An ultrasonic imaging apparatus according to this 4 third embodiment has a configuration as shown in FIG. 39, where elements which are substantially equivalent to the corresponding elements in the configuration of FIG. 35 are given the same reference numerals. This configuration of FIG. 39 differs from the configuration of FIG. 35 in that the sensitivity correction unit 31 between the DSC 30 and the D/A converter 32 is omitted, and there is provided a correction signal generator 35 which is connected with the DSC 30 and the gain controller 34.

In this configuration of FIG. 39, the image data outputted from the DSC 30 are supplied to the correction signal generator 35 as well as the D/A converter 32. The correction signal generator 35 then supplies correction signals to the gain controller 34, where the correction signals are changing according to the vector angle θ similarly as the image intensity correction function used in the second embodiment described above. The gain controller 34 then controls the gain of the high frequency amplifier 25 according to the correction signals supplied from the correction signal generator 35, so as to achieve the sensitivity correction regarding a direction perpendicular to the ultrasonic beams.

Figure 40:
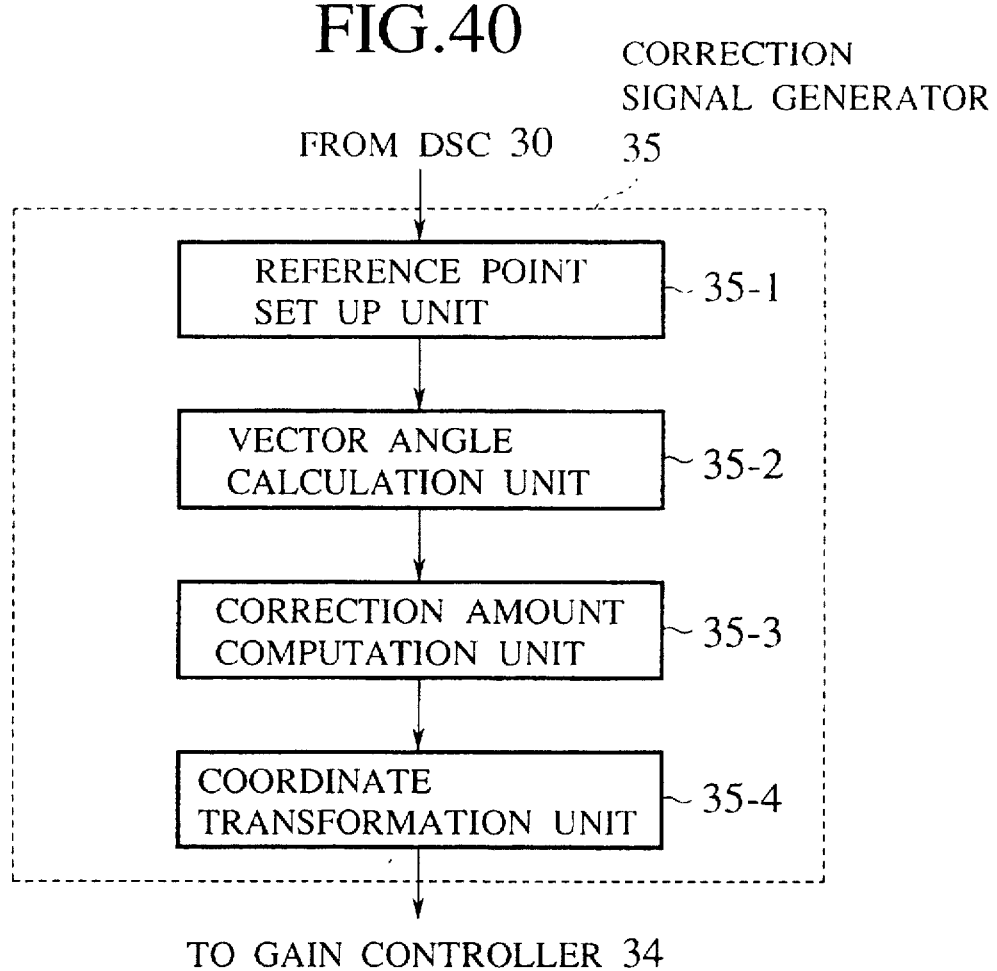
FIG. 40 is a block diagram of an internal configuration of a correction signal generator in the ultrasonic imaging apparatus of FIG. 39.

The correction signal generator 35 has an internal configuration as shown in FIG. 40, which comprises a reference point set up unit 35-1, a vector angle calculation unit 35-2, a correction amount computation unit 35-3, and coordinate transformation unit 35-4, which are connected in series, where the reference point set up unit 31-1 is connected with the DSC 30 while the coordinate transformation unit 35-4 is connected with the gain controller 34.

The reference point set up unit 35-1 sets up a reference point such as a central point of the cardiac pool for example, within a scanning plane of the ultrasonic beams. There is no specific limitation on this reference point, so that the reference point can be a center of gravity of the heart wall contour for example, or even an arbitrary point set up by an operator.

For each one of a plurality of picture elements in the scanning plane as a target point, the vector angle calculation unit 35-2 calculates a vector angle θ formed by a vector directed from the target point to the reference point and an ultrasonic beam (ultrasonic beam scanning line) vector passing through the target point.

The correction amount computation unit 35-3 computes a gain correction amount for the target point according to the vector angle θ calculated by the vector angle calculation unit 35-2.

The coordinate transformation unit 35-4 transforms the x- and y-coordinates of the target point into the coordinates on the ultrasonic beam expressed by (scanning angle, depth). The information on the transformed coordinates and the gain correction amount is then supplied as the correction signal from the correction signal generator 35 to the gain controller 34.

The gain controller 34 obtains a gain of the high frequency amplifier 25 according to the echo amplitude signals outputted from the detector 27 in order to correct the inhomogeneity of the sensitivity due to the attenuation of the ultrasonic beams, corrects the obtained gain according to the gain correction amount given from the correction signal generator 35, and controls the gain of the high frequency amplifier 25 to this corrected gain so that the echo signals will be amplified at this corrected gain.

Now, the sensitivity correction in this third embodiment will be described with reference to FIG. 41.

First, similarly as in the second embodiment described above, the reference point is set up by the reference point set up unit 35-1, and the vector angle θ formed by a vector directed from the target point to the reference point and an ultrasonic beam (ultrasonic beam scanning line) vector passing through the target point is calculated at the vector angle calculation unit 35-2.

Then, according to this vector angle θ, the correction amount for the target point regarding the gain to be corrected at the gain controller 34 with respect to the echo signals is computed by the correction amount computation unit 35-3. The information on this correction amount and the information on coordinates expressed by (scanning angle, depth) as obtained by the coordinate transformation unit 35-4 are then supplied to the gain controller 34 as the correction signal.

For the target point at coordinates (x, y), by denoting the gain for this target point before the correction as S(x, y), the gain for this target point after the correction as S'(x,y), the correction amount computation unit 35-3 computes the gain correction amount according to the following equation (11).

$$S'(x, y)=fg(\theta, S(x, y)) \tag{11}$$

where fg(θ, S(x, y)) is a gain correction-function for changing the gain according to the vector angle θ. This gain correction function fg can be given by any function which has the local maximum value for θ=90° and the local minimum value for θ=0°, 180°, and which changes its value (gain) according to θ, as shown in FIG. 41.

For example, the above equation (11) can be rewritten as the following equation (12).

$$S'(x, y)=A\times(1+B\times\sin(\theta))\times S(x, y) \tag{12}$$

where A and B are constants, and 0°≦θ≦180°.

It is also possible to use the following equation (13) instead of the above equation (12).

$$S'(x, y)=A\times(1+B\times\exp(-|\theta-90°|))\times S(x, y) \tag{13}$$

Figure 41:
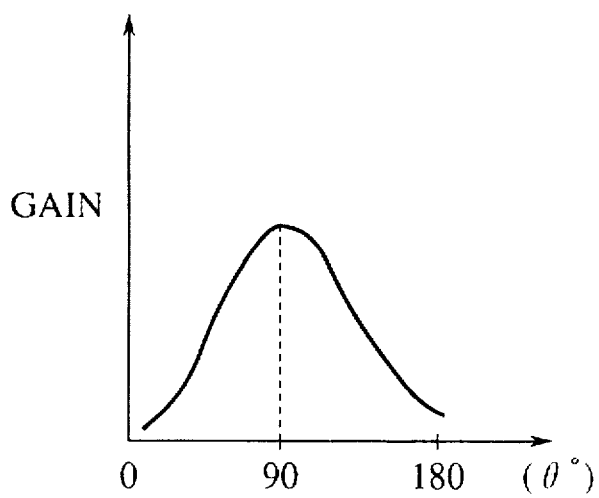
FIG. 41 is a graph showing an exemplary gain correction function used in the ultrasonic imaging apparatus of FIG. 39.

The gain correction function fg is not limited to those used in the above equations (12) and (13), and any function which changes the corrected gain according to θ as shown in FIG. 41 can be used.

Moreover, in FIG. 41, the local maximum value or the local minimum value of the corrected gain may not necessarily be constant. In other words, it is not absolutely necessary for the corrected gain S' to satisfy the relationship of S'(0°)=S'(180°).

Next, the coordinates (x, y) on the image are transformed into the coordinates (scanning angle, depth) on the ultrasonic beam at the coordinate transformation unit 35-4. Then, the information on the gain correction amount and the coordinates is supplied to the gain controller 34.

At the gain controller 34, a gain of the high frequency amplifier 25 is obtained according to the echo amplitude signals outputted from the detector 27 in order to correct the inhomogeneity of the sensitivity due to the attenuation of the ultrasonic beams, the obtained gain is corrected according to the gain correction amount given from the correction signal generator 35, and the gain of the high frequency amplifier 25 is controlled to this corrected gain so that the echo signals will be amplified at this corrected gain.

By changing the gain according to the vector angle θ as described, the sensitivity regarding a direction perpendicular to the ultrasonic beams is improved. In addition, the gain is not excessively increased for a direction parallel to the ultrasonic beams which has a good sensitivity from the beginning, so that an introduction of noise due to the excessive sensitivity correction is prevented.

Note that, in this third embodiment, the sensitivity correction is realized by the gain control with respect to the echo signals, but it is also possible to realize the sensitivity correction by controlling the gain with respect to the echo amplitude signals after the detection. This can be realized by modifying the configuration of FIG. 39 as shown in FIG. 42, where an amplitude controller 36 is additionally provided between the A/D converter 29 and the DSC 30, and the correction signals from the correction signal generator 35 are supplied to this amplitude controller 36 instead of the gain controller 34, so that the amplitude controller 36 changes the amplitudes of the echo amplitude signals according to the correction signals given from the correction signal generator 35.

Figure 42:
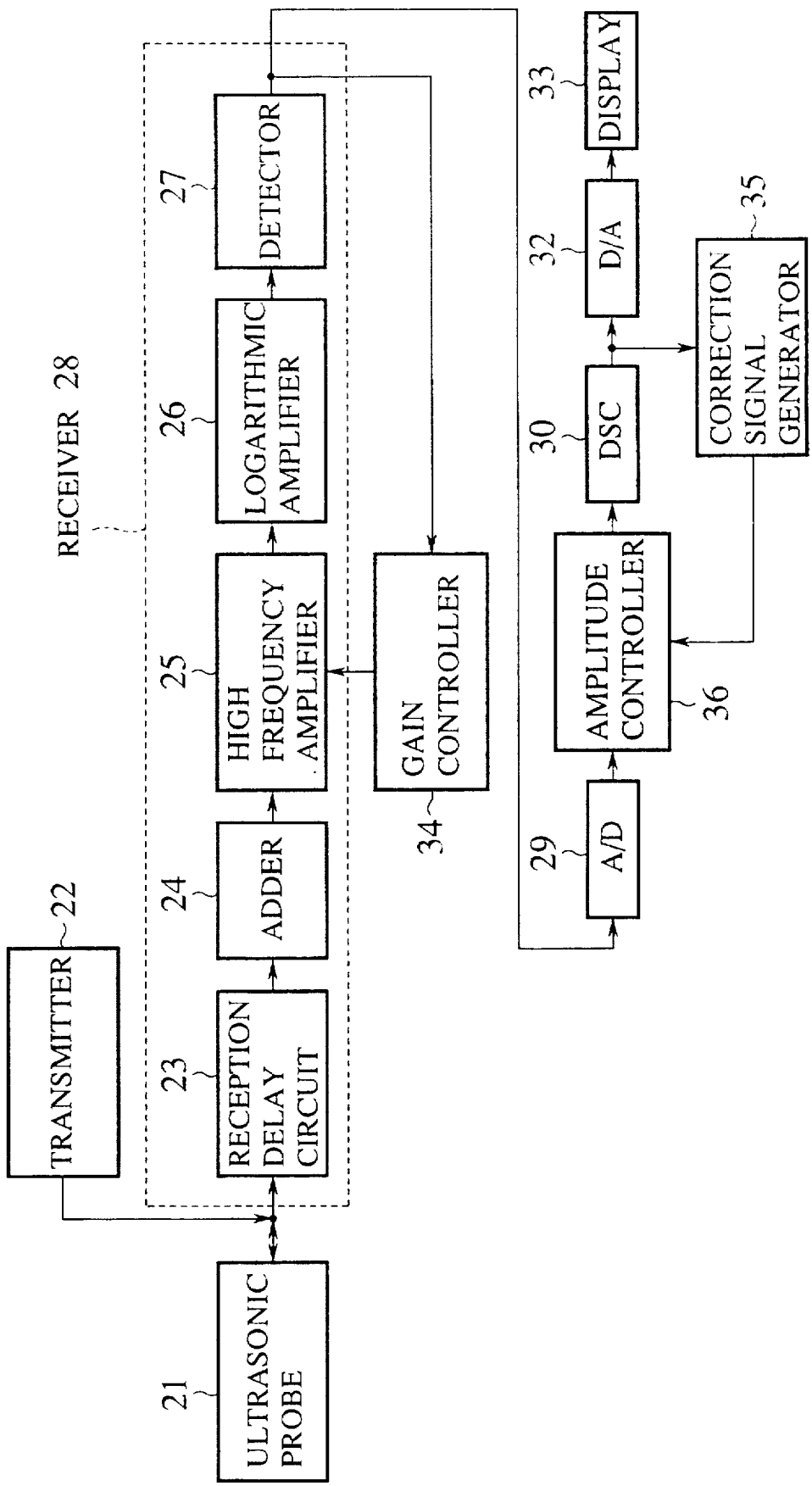
FIG. 42 is a block diagram of a modified configuration for an ultrasonic imaging apparatus according to a third embodiment of the present invention.

Note also that, in this third embodiment, the correction signal generator 35 is positioned behind the DSC 30 and the correction signal indicating the correction amount for the coordinates (x, y) is calculated and sent to the gain controller 34 of FIG. 39 or the amplitude controller 36 of FIG. 42, but it is also possible to position this correction signal generator 35 in front of the DSC 30. In such a case, the coordinate transformation unit 35-4 in the configuration of FIG. 40 becomes unnecessary in the correction signal generator 35, and the correction signal generator 35 is going to deal with the coordinates on the ultrasonic beam expressed by (scanning angle, depth) from the beginning.

Figure 43:
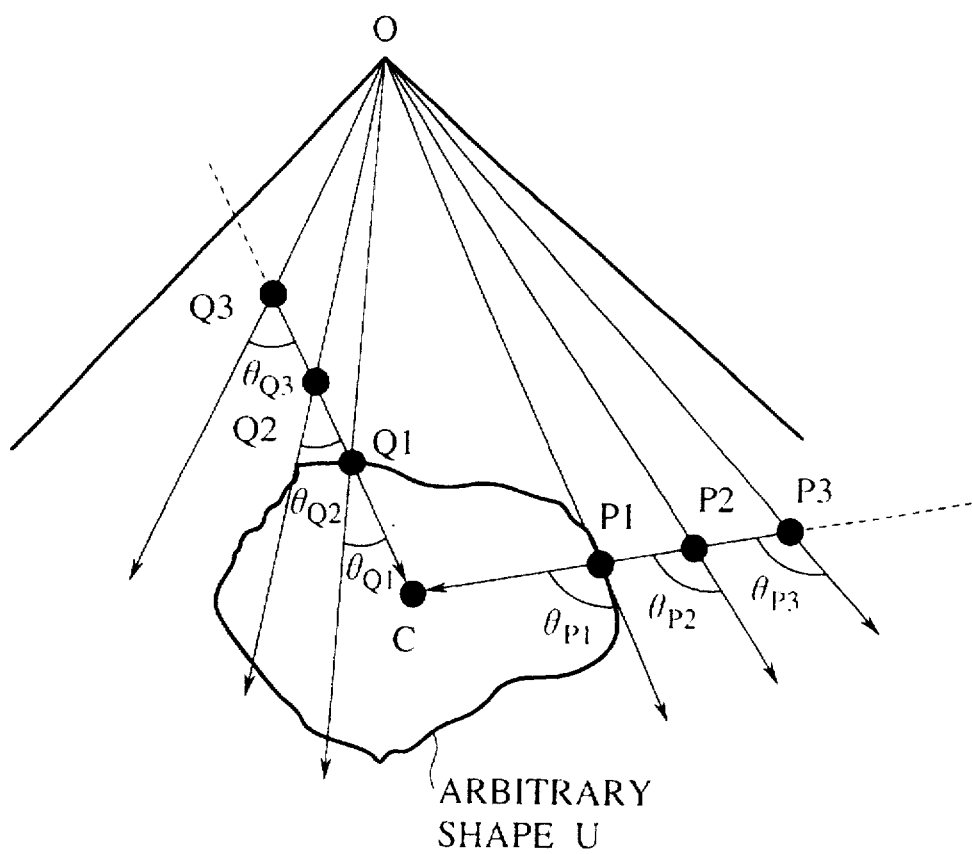
FIG. 43 is an illustration of an exemplary ultrasonic beam scanning plane in a course of operation of an ultrasonic imaging apparatus according to a fourth embodiment of the present invention.

Referring now to FIG. 43, the fourth embodiment of the present invention will be described in detail. This fourth embodiment is directed to a method and an apparatus for ultrasonic imaging, which realize the sensitivity correction regarding a direction perpendicular to the ultrasonic beam for a region outside of an arbitrary shape within the scanning plane.

In this fourth embodiment, the configuration of an ultrasonic imaging apparatus is substantially similar to that of FIG. 35 or FIG. 39. In the following, a case of using the configuration of FIG. 35 will be described.

In this fourth embodiment, an arbitrary shape U as shown in FIG. 43 such as that of the heart wall contour is set up either manually by an operator through a console (not shown), or automatically by a contour tracing function. The reference point C is set up inside this arbitrary shape U within the scanning plane by the reference point set up unit 31-1, and the vector angles $\theta_{P1}, \theta_{P2}, \ldots, \theta_{Q1}, \theta_{Q2}, \ldots$ are calculated for the target points P1, P2, ..., Q1, Q2, ..., respectively, in a region outside of the arbitrary shape U by the vector angle calculation unit 31-2. In this case, the vector angle θ is an angle formed by a first vector directed from a point on an outer edge of the arbitrary shape U (each one of points P1 and Q1 in FIG. 43) to the reference point C and an ultrasonic beam vector passing through each target point (each one of P1, P2, P3, Q1, Q2, and Q3 in FIG. 43) located on the first vector. Then, the image intensity correction according to the vector angle for each target point is carried out by the image intensity correction unit 31-3.

By limiting a region to apply the sensitivity correction only to a region outside of the arbitrary shape in this manner, a processing time can be shortened. In addition, in a case of the heart diagnosis, it is possible to emphasize only a heart wall portion which is necessary in the heart wall motion diagnosis by providing a shape similar to the heart wall contour as the arbitrary shape U in a vicinity of the heart wall contour, so that it becomes possible to realize a more accurate heart diagnosis.

Note that, in the fourth embodiment described above, the sensitivity correction is carried out for a region outside of the arbitrary shape U, but it is also possible to carry out the sensitivity correction only for points on an outer edge of the arbitrary shape U, or for a region in a vicinity of an outer edge of the arbitrary shape U.

Figure 46:
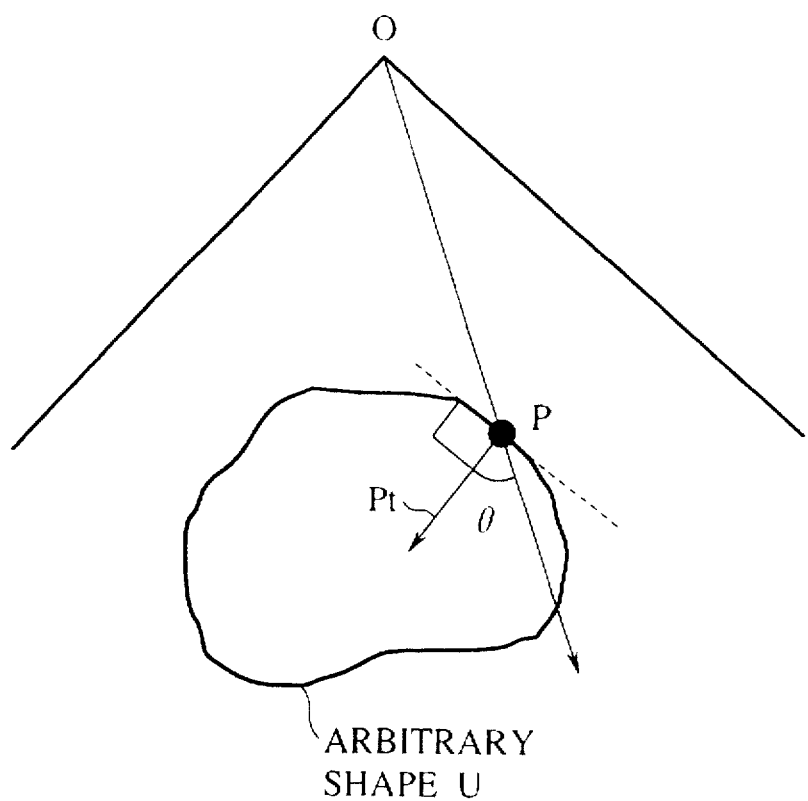
FIG. 46 is an illustration of an exemplary ultrasonic beam scanning plane in a course of operation of an ultrasonic imaging apparatus according to a fifth embodiment of the present invention.

Referring now to FIG. 44 through FIG. 46, the fifth of the present invention will be described in detail. This fourth embodiment is directed to a method and an apparatus for ultrasonic imaging, which realize the sensitivity correction regarding a direction perpendicular to the ultrasonic beam by calculating the vector angle without using the reference point.

In this fifth embodiment, the configuration of an ultrasonic imaging apparatus is substantially similar to that of FIG. 35 or FIG. 39, except that the internal configuration of the sensitivity correction unit 31 in FIG. 35 should be modified as shown in FIG. 44, or the internal configuration of the correction signal generator 35 in FIG. 39 should be modified as shown in FIG. 45.

Namely, in the modified configuration of FIG. 44, the reference point set up unit 31-1 of FIG. 36 is replaced by a perpendicular line vector calculation unit 31-4 while the rest is the same as in FIG. 36. Also, in the modified configuration of FIG. 45, the reference point set up unit 35-1 of FIG. 40 is replaced by a perpendicular line vector calculation unit 35-5 while the rest is the same as in FIG. 40.

Now, a method for calculating the vector angle without using the reference point will be described with reference to FIG. 46. The perpendicular line vector calculation unit 31-4 or 35-5 obtains a perpendicular line Pt which is passing through the target point P on an outer edge of the arbitrary shape U and perpendicular to a contour of the arbitrary shape U. Then, the vector angle calculation unit 31-2 or 35-2 obtains the vector angle θ formed by this perpendicular line Pt and an ultrasonic beam vector OP passing through the target point P. The image intensity correction unit 31-3 then carries out the image intensity correction (sensitivity correction) according to this vector angle θ with respect to the image data, or the correction amount computation unit 35-3 obtains the gain correction amount according to this vector angle θ.

Also, similarly as in the fourth embodiment described above, it is also possible in this fifth embodiment to carry out the sensitivity correction to an entire region outside of the arbitrary shape U, or only to a region in a vicinity of the arbitrary shape U.

As described, according to the second to fifth embodiments of the present invention, the reception gain or the image intensity of the image at a particular position is adjusted and corrected according to an angle formed by a vector set up at that particular position and an ultrasonic beam vector passing through that particular position. Consequently, it is possible to provide a method and an apparatus for ultrasonic imaging, which are capable of obtaining the ultrasonic image in high precision by correcting the sensitivity in a direction perpendicular to the ultrasonic beams.

It is to be noted that, in the second to fifth embodiments described above, the vector angle calculation and the sensitivity correction amount calculation are carried out for each picture element separately, but it is also possible to the vector angle calculation and the sensitivity correction amount calculation for only one picture element among a plurality of picture elements having similar vector angles, and use the same sensitivity correction amount for all these plurality of picture elements having similar vector angles.

Figure 47:
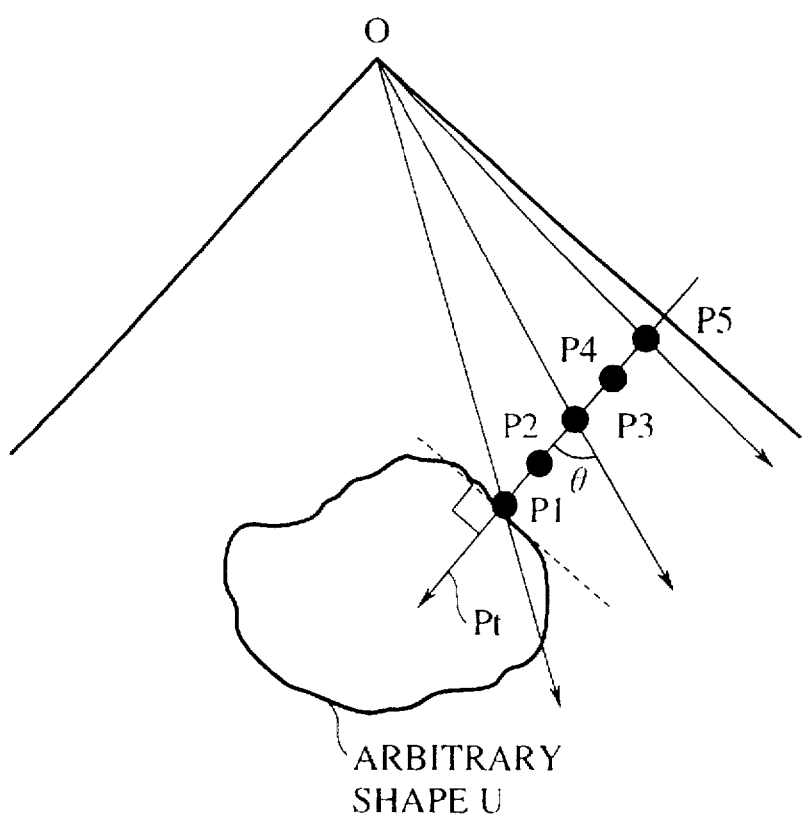
FIG. 47 is an illustration of an exemplary ultrasonic beam scanning plane in a course of one possible modified operation of an ultrasonic imaging apparatus according to a fifth embodiment of the present invention.

For example, FIG. 47 shows this modification for a case of carrying out the sensitivity correction according to the vector angle formed by the perpendicular line Pt and the ultrasonic beam vector at the target point P1 on the arbitrary shape U as in a case of FIG. 46. In FIG. 47, five target points P1 and P5 are provided on the perpendicular line Pt passing through the target point P1 on the contour of the arbitrary shape U. In this case, all these target points P1 to P5 are regarded as a single region, and the vector angle θ is calculated by using the ultrasonic-beam vector OP3 passing through the target point P3 among these target points P1 to P5. Then, the sensitivity correction according to this vector angle θ is carried out to all of the target points P1 to P5. In other words, the same correction amount is used for all the target points P1 to P5 which are regarded as the same region. In this manner, it is possible to reduce the amount of calculations required in the sensitivity correction, and thereby realize the shorter processing time for the sensitivity correction.

It is also to be noted that, in the second to fourth embodiment described above, the set up of the reference point by the sensitivity correction unit 31 or the correction signal generator 35 can be done either automatically by the apparatus, or according to a manually entered user's specification.

Figure 48:
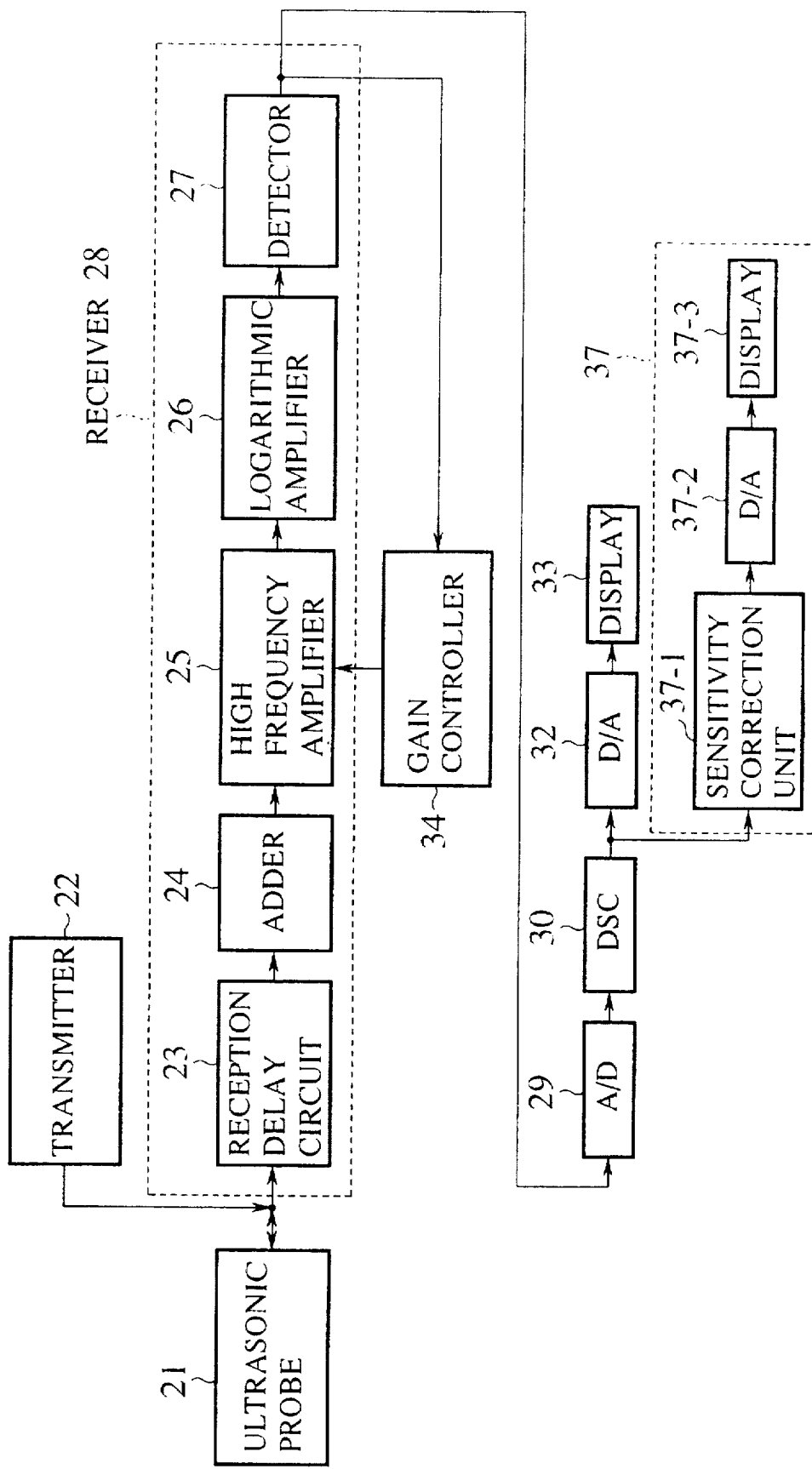
FIG. 48 is a block diagram of one possible modified configuration for an ultrasonic imaging apparatus according to second to fifth embodiments of the present invention.

It is also to be noted that, in the second to fifth embodiment described above, the sensitivity correction according to the present invention is carried out inside the ultrasonic imaging apparatus, but as shown in FIG. 48, it is also possible to carry out the sensitivity correction at an external sensitivity correction device 37 which is provided separately from the ultrasonic imaging apparatus and to which the output signals of the ultrasonic imaging apparatus are supplied.

This external sensitivity correction device 37 includes a sensitivity correction unit 37-1, a D/A converter 37-2 and a display 37-3 which are similar to the sensitivity correction unit 31, the D/A converter 32 and the display 33 of FIG. 35. Here, however, it is not absolutely necessary for the external sensitivity correction device 37 to incorporate the display 37-3, and it is also possible to use a configuration in which the output of the external sensitivity correction device 37 can be supplied to the ultrasonic imaging apparatus and displayed on the display 33 of the ultrasonic imaging apparatus side.

In a case of using this configuration of FIG. 48, the data input to the external sensitivity correction device 37 may be realized by recording the output signals of the ultrasonic imaging apparatus in some recording medium once, and reading out the necessary data from that recording medium.

It is also to be noted that the above described embodiments according to the present invention may be conveniently implemented using a conventional general purpose digital computer programmed according to the teachings of the present specification, as will be apparent to those skilled in the computer art. Appropriate software coding can readily be prepared by skilled programmers based on the teachings of the present disclosure, as will be apparent to those skilled in the software art.

Such a software package can be a computer program product which employs a storage medium including stored computer code which is used to program a computer to perform the disclosed function and process of the present invention. The storage medium may include, but is not limited to, any type of conventional floppy disks, optical disks, CD-ROMs, magneto-optical disks, ROMs, RAMs, EPROMs, EEPROMs, magnetic or optical cards, or any other suitable media for storing electronic instructions.

It is also to be noted that, besides those already mentioned above, many modifications and variations of the above embodiments may be made without departing from the novel and advantageous features of the present invention. Accordingly, all such modifications and variations are intended to be included within the scope of the appended claims.

What is claimed is:

1. A method for processing an ultrasonic image of a long axis view of a heart imaged from an apex portion side, comprising the steps of:

extracting a heart wall contour from the ultrasonic image;

determining a center of gravity of the heart wall contour extracted by the extracting step; and detecting an annulus portion of the heart from a plurality of points on the heart wall contour located at positions deeper than the center of gravity determined by the determining step, according to a prescribed criterion regarding said plurality of points.

2. The method of claim 1, wherein the detecting step detects the annulus portion according to the prescribed criterion regarding at least one of a curvature of the heart wall contour at each of said plurality of points, a distance between an apex portion on the ultrasonic image and each of said plurality of points, a distance between an ultrasonic beam transmission/reception position on the ultrasonic image and each of said plurality of points, a distance between the center of gravity and each of said plurality of points, a distance between an edge of an ultrasonic beam scanning range on the ultrasonic image and each of said plurality of points, and a distance between an edge of a display screen displaying the ultrasonic image and each of said plurality of points.

3. The method of claim 1, further comprising the step of:

calculating a cardiac function information for the heart according to the annulus portion detected by the detecting step.

4. A method for processing an ultrasonic image of a long axis view of a heart imaged by a transesophageal echocardiography, comprising the steps of:

extracting a heart wall contour from the ultrasonic image;

determining a center of gravity of the heart wall contour extracted by the extracting step; and detecting an annulus portion of the heart from a plurality of points on the heart wall contour located at positions shallower than the center of gravity determined by the determining step, according to a prescribed criterion regarding said plurality of points.

5. The method of claim 4, wherein the detecting step detects the annulus portion according to the prescribed criterion regarding at least one of a curvature of the heart wall contour at each of said plurality of points, a distance between an apex portion on the ultrasonic image and each of said plurality of points, a distance between an ultrasonic beam transmission/reception position on the ultrasonic image and each of said plurality of points, a distance between the center of gravity and each of said plurality of points, a distance between an edge of an ultrasonic beam scanning range on the ultrasonic image and each of said plurality of points, and a distance between an edge of a display screen displaying the ultrasonic image and each of said plurality of points.

6. The method of claim 4, further comprising the step of:

calculating a cardiac function information for the heart according to the annulus portion detected by the detecting step.

7. A method for processing an ultrasonic image of a long axis view of a heart, comprising the steps of:

extracting a heart wall contour from the ultrasonic image;

determining a center of gravity of the heart wall contour extracted by the extracting step; and detecting an annulus portion of the heart from a plurality of points on the heart wall contour located at positions father away from an apex portion on the heart wall contour than the center of gravity determined by the determining step, according to a prescribed criterion regarding said plurality of points.

8. The method of claim 7, wherein the detecting step detects the annulus portion according to the prescribed criterion regarding at least one of a curvature of the heart wall contour at each of said plurality of points, a distance between the apex portion on the ultrasonic image and each of said plurality of points, a distance between an ultrasonic beam transmission/reception position on the ultrasonic image and each of said plurality of points, a distance between the center of gravity and each of said plurality of points, a distance between an edge of an ultrasonic beam scanning range-on the ultrasonic image and each of said plurality of points, and a distance between an edge of a display screen displaying the ultrasonic image and each of said plurality of points.

9. The method of claim 7, further comprising the step of:

calculating a cardiac function information for the heart according to the annulus portion detected by the detecting step.

10. An apparatus for processing an ultrasonic image of a long axis view of a heart imaged from an apex portion side, comprising:

means for extracting a heart wall contour from the ultrasonic image;

means for determining a center of gravity of the heart wall contour extracted by the extracting means; and means for detecting an annulus portion of the heart from a plurality of points on the heart wall contour located at positions deeper than the center of gravity determined by the determining means, according to a prescribed criterion regarding said plurality of points.

11. The apparatus of claim 10, wherein the detecting means detects the annulus portion according to the prescribed criterion regarding at least one of a curvature of the heart wall contour at each of said plurality of points, a distance between an apex portion on the ultrasonic image and each of said plurality of points, a distance between an ultrasonic beam transmission/reception position on the ultrasonic image and each of said plurality of points, a distance between the center of gravity and each of said plurality of points, a distance between an edge of an ultrasonic beam scanning range on the ultrasonic image and each of said plurality of points, and a distance between an edge of a display screen displaying the ultrasonic image and each of said plurality of points.

12. The apparatus of claim 10, further comprising:

means calculating a cardiac function information for the heart according to the annulus portion detected by the detecting means.

13. An apparatus for processing an ultrasonic image of a long axis view of a heart imaged by a transesophageal echocardiography, comprising:

means for extracting a heart wall contour from the ultrasonic image;

means for determining a center of gravity of the heart wall contour extracted by the extracting means; and means for detecting an annulus portion of the heart from a plurality of points on the heart wall contour located at positions shallower than the center of gravity determined by the determining means, according to a prescribed criterion regarding said plurality of points.

14. The apparatus of claim 13, wherein the detecting means detects the annulus portion according to the prescribed criterion regarding at least one of a curvature of the heart wall contour at each of said plurality of points, a distance between an apex portion on the ultrasonic image and each of said plurality of points, a distance between an ultrasonic beam transmission/reception position on the ultrasonic image and each of said plurality of points, a distance between the center of gravity and each of said plurality of points, a distance between an edge of an ultrasonic beam scanning range on the ultrasonic image and each of said plurality of points, and a distance between an edge of a display screen displaying the ultrasonic image and each of said plurality of points.

15. The apparatus of claim 13, further comprising:

means for calculating a cardiac function information for the heart according to the annulus portion detected by the detecting means.

16. An apparatus for processing an ultrasonic image of a long axis view of a heart, comprising:

means for extracting a heart wall contour from the ultrasonic image;

means for determining a center of gravity of the heart wall contour extracted by the extracting means; and means for detecting an annulus portion of the heart from a plurality of points on the heart wall contour located at positions father away from an apex portion on the heart wall contour than the center of gravity determined by the determining means, according to a prescribed criterion regarding said plurality of points.

17. The apparatus of claim 16, wherein the detecting means detects the annulus portion according to the prescribed criterion regarding at least one of a curvature of the heart wall contour at each of said plurality of points, a distance between the apex portion on the ultrasonic image and each of said plurality of points, a distance between an ultrasonic beam transmission/reception position on the ultrasonic image and each of said plurality of points, a distance between the center of gravity and each of said plurality of points, a distance between an edge of an ultrasonic beam scanning range on the ultrasonic image and each of said plurality of points, and a distance between an edge of a display screen displaying the ultrasonic image and each of said plurality of points.

18. The apparatus of claim 16, further comprises:

means for calculating a cardiac function information for the heart according to the annulus portion detected by the detecting means.

19. A method for imaging an ultrasonic image, comprising the steps of:

obtaining an ultrasonic image of an object to be imaged by applying an ultrasonic beam to the object and receiving a reflected beam from the object; and adjusting a reception gain used by the obtaining step at specific positions within a scanning space scanned by the ultrasonic beam, according to an angle formed by an ultrasonic beam vector defined by the ultrasonic beam passing through each specific position and a prescribed vector defined at each specific position.

20. The method of claim 19, wherein the prescribed vector is a vector pointing from each specific point to a reference point set up in advance within the scanning space.

21. The method of claim 19, wherein each specific point is a point which is located on a prescribed shape set up in advance within the scanning space, and the prescribed vector is a vector pointing perpendicularly with respect to the prescribed shape at each specific point.

22. A method for imaging an ultrasonic image, comprising the steps of:

obtaining an ultrasonic image of an object to be imaged by applying an ultrasonic beam to the object and receiving a reflected beam from the object; and correcting an image intensity of the ultrasonic image obtained by the obtaining step at specific positions within a scanning space scanned by the ultrasonic beam, according to an angle formed by an ultrasonic beam vector defined by the ultrasonic beam passing through each specific position and a prescribed vector defined at each specific position.

23. The method of claim 22, wherein the prescribed vector is a vector pointing from each specific point to a reference point set up in advance within the scanning space.

24. The method of claim 22, wherein each specific point is a point which is located on a prescribed shape set up in advance within the scanning space, and the prescribed vector is a vector pointing perpendicularly with respect to the prescribed shape at each specific point.

25. An apparatus for imaging an ultrasonic image, comprising:

means for obtaining an ultrasonic image of an object to be imaged by applying an ultrasonic beam to the object and receiving a reflected beam from the object; and means adjusting a reception gain used by the obtaining means at specific positions within a scanning space scanned by the ultrasonic beam, according to an angle formed by an ultrasonic beam vector defined by the ultrasonic beam passing through each specific position and a prescribed vector defined at each specific position.

26. The apparatus of claim 25, wherein the prescribed vector is a vector pointing from each specific point to a reference point set up in advance within the scanning space.

27. The apparatus of claim 25, wherein each specific point is a point which is located on a prescribed shape set up in advance within the scanning space, and the prescribed vector is a vector pointing perpendicularly with respect to the prescribed shape at each specific point.

28. An apparatus for imaging an ultrasonic image, comprising:

means for obtaining an ultrasonic image of an object to be imaged by applying an ultrasonic beam to the object and receiving a reflected beam from the object; and means for correcting an image intensity of the ultrasonic image obtained by the obtaining means at specific positions within a scanning space scanned by the ultrasonic beam, according to an angle formed by an ultrasonic beam vector defined by the ultrasonic beam passing through each specific position and a prescribed vector defined at each specific position.

29. The apparatus of claim 28, wherein the prescribed vector is a vector pointing from each specific point to a reference point set up in advance within the scanning space.

30. The apparatus of claim 28, wherein each specific point is a point which is located on a prescribed shape set up in advance within the scanning space, and the prescribed vector is a vector pointing perpendicularly with respect to the prescribed shape at each specific point.

31. An article of manufacture, comprising:

a computer usable medium having computer readable program code means embodied therein for causing a computer to function as a system for processing an ultrasonic image of a long axis view of a heart imaged from an apex portion side, the computer readable program code means including:

first computer readable program code means for causing said computer to extract a heart wall contour from the ultrasonic image;

second computer readable program code means for causing said computer to determine a center of gravity of the heart wall contour extracted by the first computer readable program code means; and third computer readable program code means for causing said computer to detect an annulus portion of the heart from a plurality of points on the heart wall contour located at positions deeper than the center of gravity determined by the second computer readable program code means, according to a prescribed criterion regarding said plurality of points.

32. An article of manufacture, comprising:

a computer usable medium having computer readable program code means embodied therein for causing a computer to function as a system for processing an ultrasonic image of a long axis view of a heart imaged by a transesophasgeal echocardiography, the computer readable program code means including:

first computer readable program code means for causing said computer to extract a heart wall contour from the ultrasonic image;

second computer readable program code means for causing said computer to determine a center of gravity of the heart wall contour extracted by the first computer readable program code means; and third computer readable program code means for causing said computer to detect an annulus portion of the heart from a plurality of points on the heart wall contour located at positions shallower than the center of gravity determined by the second computer readable program code means, according to a prescribed criterion regarding said plurality of points.

33. An article of manufacture, comprising:

a computer usable medium having computer readable program code means embodied therein for causing a computer to function as a system for processing an ultrasonic image of a long axis view of a heart, the computer readable program code means including:

first computer readable program code means for causing said computer to extract a heart wall contour from the ultrasonic image;

second computer readable program code means for causing said computer to determine a center of gravity of the heart wall contour extracted by the first computer readable program code means; and third computer readable program code means for causing said computer to detect an annulus portion of the heart from a plurality of points on the heart wall contour located at positions father away from an apex portion on the heart wall contour than the center of gravity determined by the second computer readable program code means, according to a prescribed criterion regarding said plurality of points.

34. An article of manufacture, comprising:

a computer usable medium having computer readable program code means embodied therein for causing a computer to function as a system for controlling an imaging of an ultrasonic image, the computer readable program code means including:

first computer readable program code means for causing said computer to obtain an ultrasonic image of an object to be imaged by applying an ultrasonic beam to the object and receiving a reflected beam from the object; and second computer readable program code means for causing said computer to adjust a reception gain used by the first computer readable program code means at specific positions within a scanning space scanned by the ultrasonic beam, according to an angle formed by an ultrasonic beam vector defined by the ultrasonic beam passing through each specific position and a prescribed vector defined at each specific position.

35. An article of manufacture, comprising:

a computer usable medium having computer readable program code means embodied therein for causing a computer to function as a system for controlling an imaging of an ultrasonic image, the computer readable program code means including:

first computer readable program code means for causing said computer to obtain an ultrasonic image of an object to be imaged by applying an ultrasonic beam to the object and receiving a reflected beam from the object; and second computer readable program code means for causing said computer to correct an image intensity of the ultrasonic image obtained by the first computer readable program code means at specific positions within a scanning space scanned by the ultrasonic beam, according to an angle formed by an ultrasonic beam vector defined by the ultrasonic beam passing through each specific position and a prescribed vector defined at each specific position.

* * * * *

UNITED STATES PATENT AND TRADEMARK OFFICE
CERTIFICATE OF CORRECTION

PATENT NO.  : 5,797,844
DATED       : August 25, 1998
INVENTOR(S) : Hideki YOSHIOKA et al.

It is certified that error appears in the above-identified patent and that said Letters Patent is hereby corrected as shown below:

ON THE COVER PAGE, at Item [30] Foreign Application Priority Data, please insert --September 6, 1995, [JP] Japan, 7-229042--.

Signed and Sealed this

Eighteenth Day of May, 1999

Attest:

Q. TODD DICKINSON

Attesting Officer

Acting Commissioner of Patents and Trademarks